United States Patent
Mathers et al.

(10) Patent No.: US 9,989,528 B2
(45) Date of Patent: Jun. 5, 2018

(54) SYNTHETIC OLGONONUCLEOTIDES FOR DETECTION OF NUCLEIC ACID BINDING PROTEINS

(71) Applicants: William Mathers, Lake Oswego, OR (US); Zheng Ye, Portland, OR (US)

(72) Inventors: William Mathers, Lake Oswego, OR (US); Zheng Ye, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 278 days.

(21) Appl. No.: 14/471,403

(22) Filed: Aug. 28, 2014

(65) Prior Publication Data

US 2015/0065378 A1    Mar. 5, 2015

Related U.S. Application Data

(60) Provisional application No. 61/870,904, filed on Aug. 28, 2013.

(51) Int. Cl.
*C12Q 1/68* (2018.01)
*G01N 33/561* (2006.01)

(52) U.S. Cl.
CPC ............ *G01N 33/561* (2013.01); *C12Q 1/68* (2013.01); *C12Q 1/686* (2013.01)

(58) Field of Classification Search
None
See application file for complete search history.

(56) References Cited

U.S. PATENT DOCUMENTS

| | | | |
|---|---|---|---|
| 6,066,452 A | 5/2000 | Weissman et al. | |
| 6,337,186 B1 * | 1/2002 | Krebber | C12N 15/1027 435/183 |
| 7,122,317 B2 | 10/2006 | Clausen et al. | |
| 8,496,798 B2 | 7/2013 | Ye et al. | |
| 2002/0052333 A1 * | 5/2002 | Dzau | A61K 31/70 514/44 R |
| 2003/0104368 A1 | 6/2003 | Zhou | |
| 2003/0215854 A1 | 11/2003 | Clausen | |
| 2004/0191781 A1 * | 9/2004 | Zhang | G06F 19/18 435/6.14 |

FOREIGN PATENT DOCUMENTS

WO    WO 2008-147899    12/2008

OTHER PUBLICATIONS

Guieysse, A. L. et al., "Identification of a triplex DNA-binding protein from human cells," *J. Mol. Biol.*, Mar. 28, 1997, vol. 267, No. 2, pp. 289-298.

International Search Report and Written Opinion issued by the Korean Intellectual Property Office dated Dec. 15, 2014, for corresponding PCT Patent Application No. PCT/US2014/053183, 12 pp.

* cited by examiner

*Primary Examiner* — James S Ketter
(74) *Attorney, Agent, or Firm* — Klarquist Sparkman, LLP

(57) ABSTRACT

Synthetic oligonucleotides that comprise a nucleic acid binding protein binding site, PCR primer sequences, and tag sequences that do not bind to nucleic acid binding proteins, with a total length of 85-130 nucleotides are disclosed herein. Also disclosed are libraries and kits comprising the synthetic oligonucleotides as well as methods of detecting nucleic acid binding proteins in a sample using the synthetic oligonucleotides.

20 Claims, 1 Drawing Sheet

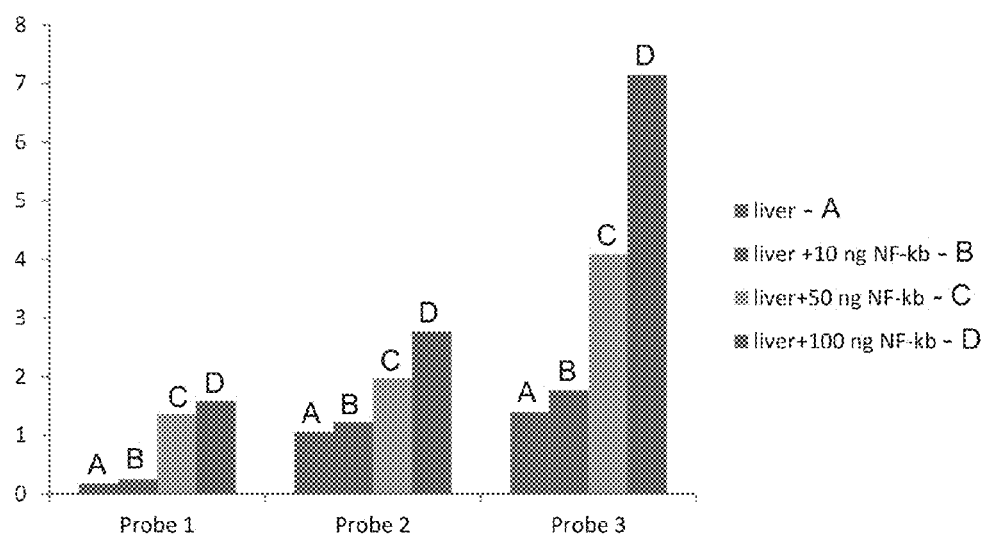

US 9,989,528 B2

SYNTHETIC OLGONONUCLEOTIDES FOR DETECTION OF NUCLEIC ACID BINDING PROTEINS

CROSS REFERENCE TO RELATED APPLICATION

The present application claims the benefit of U.S. Provisional Patent Application No. 61/870,904, entitled "SYNTHETIC OLIGONUCLEOTIDES FOR DETECTION OF NUCLEIC ACID BINDING PROTEINS," filed Aug. 28, 2013, the disclosure of which is incorporated herein by reference in its entirety.

FIELD

Generally, the field is nucleic acid probes and arrays thereof. More specifically, the field is nucleic acid probes that can detect, identify, and quantify nucleic acid binding proteins in a sample.

BACKGROUND

Nucleic acid binding proteins are proteins in the nucleus that bind to nucleic acids such as DNA and RNA to perform any of a number of activities, including the promotion or inhibition of RNA transcription or protein translation. Their binding can be identified with DNA probes that are separated and rendered visible by gel electrophoresis but their detection is limited to one or several binding proteins at one time. Using current methods, it is difficult to quantify nucleic acid binding proteins present in a biological sample. Many currently available technologies comprise the use of probes that self-hybridize, therefore reducing specificity and ease of use. Clearly, new probes that identify nucleic acid binding proteins in biological samples are necessary.

SUMMARY

Disclosed herein are synthetic oligonucleotides that identify DNA binding proteins in a sample. This includes methods of using said oligonucleotides to measure the binding action of a plurality of DNA binding proteins by binding the oligonucleotides to a microarray chip.

The synthetic oligonucleotide comprises sequences that include a nucleic acid binding protein binding site, a sequence that is an RNA polymerase promoter or a binding site for a PCR primer, and a tag sequence that does not bind any nucleic acid binding protein. At least the nucleic acid binding protein binding site is double stranded and the entire synthetic oligonucleotide can be double stranded. The probe is between 85 and 130 base pairs in length, including between 90 and 98 nucleotides in length. The sequence may comprise T7, SP6, or T5 promoters including SEQ ID NO: 1 and SEQ ID NO: 2. In some examples, the tag sequence is any of SEQ ID NOs: 3-98.

Further disclosed are sets of synthetic oligonucleotides each with different nucleic acid binding protein binding sites as well as kits comprising sets of synthetic oligonucleotides and microarrays comprising oligonucleotides complementary to the tag sequences. The oligonucleotides on the microarray are addressable.

Also disclosed is a method of detecting a DNA binding protein in a sample involving contacting one of the disclosed synthetic oligonucleotides with a sample. The sample is then subjected to conditions that allow binding of any DNA binding proteins in the sample to the synthetic oligonucleotides to form protein/oligonucleotide complexes. The protein/oligonucleotide complexes are purified by electrophoresis. The oligonucleotides are labeled and hybridized to an array. Detection of the label within the context of the array indicates the presence of the DNA binding protein in the sample. The label may be any label, including a fluorescent label. The label may be incorporated into the oligonucleotide by any method including method involving use of RNA polymerase or polymerase chain reaction. Electrophoresis may be performed using any device or method including the devices and methods described in US2012/0160683 which is hereby incorporated by reference in its entirety.

The foregoing and other objects, features, and advantages of the invention will become more apparent from the following detailed description, which proceeds with reference to the accompanying FIGURE and sequence listing.

BRIEF DESCRIPTION OF THE DRAWING

FIG. 1 is a bar graph of the relative strength (Y axis) of three different probes (Probe 1—SEQ ID NO: 197) (Probe 2—SEQ ID NO: 198) and Probe 3—SEQ ID NO: 99 incubated with nuclear extracts comprising the indicated amounts of added nuclear factor kappa-light-chain enhance of activated B cells (NF-κB), purified by electrophoresis, and bound to a microarray as described herein.

BRIEF DESCRIPTION OF SEQUENCES

The nucleic acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. All sequence database accession numbers referenced herein are understood to refer to the version of the sequence identified by that accession number as it was available on the designated date. In the accompanying sequence listing:

SEQ ID NO: 1 is a universal forward primer sequence binding site.

SEQ ID NO: 2 is a universal reverse primer sequence binding site.

SEQ ID NOs: 3-98 are examples of tag sequences

SEQ ID NOs: 99-100 are synthetic oligonucleotide probes that can bind NF-κB

SEQ ID NOs: 101-102 are synthetic oligonucleotide probes that can bind P53.

SEQ ID NOs: 103-104 are synthetic oligonucleotide probes that can bind AR (androgen receptor).

SEQ ID NOs: 105-106 are synthetic oligonucleotide probes that can bind Creb.

SEQ ID NOs: 107-108 are synthetic oligonucleotide probes that can bind activator protein 1 (AP-1).

SEQ ID NOs: 109-110 are synthetic oligonucleotide probes that can bind early growth response protein 1(EGR-1).

SEQ ID NOs: 111-112 are synthetic oligonucleotide probes that can bind activating protein 2 (AP-2).

SEQ ID NOs: 113-114 are synthetic oligonucleotide probes that can bind Nkx-3.1.

SEQ ID NOs: 115-116 are synthetic oligonucleotide probes that can bind prostate-specific antigen (PSA).

SEQ ID NOs: 117-118 are synthetic oligonucleotide probes that can bind C-myb.

SEQ ID NOs: 119-120 are synthetic oligonucleotide probes that can bind peroxisome proliferator-activated receptor (PPAR).

SEQ ID NOs: 121-122 are synthetic oligonucleotide probes that can bind PPAR gamma.

SEQ ID NOs: 123-124 are synthetic oligonucleotide probes that can bind Oct-1.

SEQ ID NOs: 125-126 are synthetic oligonucleotide probes that can bind hypoxia-inducible factor 1 alpha (HIF-1α).

SEQ ID NOs: 127-128 are synthetic oligonucleotide probes that can bind E2F transcription factor 1 (E2F-1).

SEQ ID NOs: 129-130 are synthetic oligonucleotide probes that can bind CEBP (CCAAT-enhancer binding protein).

SEQ ID NOs: 131-132 are synthetic oligonucleotide probes that can bind B-cell lymphoma 6 (Bcl-6).

SEQ ID NOs: 133-134 are synthetic oligonucleotide probes that can bind SRE (sterol regulatory element).

SEQ ID NOs: 135-136 are synthetic oligonucleotide probes that can bind Oxo3a.

SEQ ID NOs: 137-138 are synthetic oligonucleotide probes that can bind forkhead box a (Foxa).

SEQ ID NO: 139 and 140 are synthetic oligonucleotide probes that can bind forkhead box o (Foxo).

SEQ ID NOs: 141 and 142 are synthetic oligonucleotide probes that can bind PR (progesterone receptor).

SEQ ID NOs: 143 and 144 are synthetic oligonucleotide probes that can bind RAR (retinoic acid receptor).

SEQ ID NOs: 145 and 146 are synthetic oligonucleotide probes that can bind Snai1.

SEQ ID NOs: 147 and 148 are synthetic oligonucleotide probes that can bind Stat1.

SEQ ID NOs: 149 and 150 are synthetic oligonucleotide probes that can bind Stat3.

SEQ ID NOs: 151 and 152 are synthetic oligonucleotide probes that can bind Stat4.

SEQ ID NOs: 153 and 154 are synthetic oligonucleotide probes that can bind Stat5.

SEQ ID NOs: 155 and 156 are synthetic oligonucleotide probes that can bind Stat5 and Stat6.

SEQ ID NOs: 157 and 158 are synthetic oligonucleotide probes that can bind Brn-3.

SEQ ID NOs: 159 and 160 are synthetic oligonucleotide probes that can bind CBF (CCAAT binding factor).

SEQ ID NOs: 161 and 162 are synthetic oligonucleotide probes that can bind CDP (CCAAT displacement protein).

SEQ ID NOs: 163 and 164 are synthetic oligonucleotide probes that can bind CCCTC-binding factor (CTCF).

SEQ ID NO: 165 and 166 are synthetic oligonucleotide probes that can bind Fast-1.

SEQ ID NOs: 167 and 168 are synthetic oligonucleotide probes that can bind GATA binding protein 2 (GATA2).

SEQ ID NOs: 169 and 170 are synthetic oligonucleotide probes that can bind runt-related transcription factor 3 (RUNX3).

SEQ ID NOs: 171 and 172 are synthetic oligonucleotide probes that can bind ETS-related gene (ERG).

SEQ ID NOs: 173 and 174 are synthetic oligonucleotide probes that can bind FLI-1 (Friend leukemia virus integration 1).

SEQ ID NOs: 175 and 176 are synthetic oligonucleotide probes that can bind hepatocyte nuclear factor 4 (HNF-4).

SEQ ID NOs: 177 and 178 are synthetic oligonucleotide probes that can bind IRF-1 (interferon regulatory factor 1).

SEQ ID NOs: 179 and 180 is a synthetic oligonucleotide probe that can bind nuclear factor 1 (NF-1).

SEQ ID NOs: 181 and 182 are synthetic oligonucleotide probes that can bind nuclear factor, erythroid 2 (NF-e2).

SEQ ID NOs: 183 and 184 are synthetic oligonucleotide probes that can bind upstream stimulatory factor (USF-1).

SEQ ID NO: 185 is a synthetic oligonucleotide probe that can bind Interferon-Gamma Activated Sequence (GAS)/Interferon-Stimulated Response Element (ISRE).

SEQ ID NO: 186 is a synthetic oligonucleotide probe that can bind Smad.

SEQ ID NOs: 187-188 are synthetic oligonucleotide probes that can bind Smad.

SEQ ID NO: 189-192 are synthetic oligonucleotide probes that lack a nucleic acid binding protein binding site used as negative controls.

SEQ ID NOs: 193 and 194 are synthetic oligonucleotide probes that can bind Myc-Max.

SEQ ID NO: 195 is a T7 promoter site

SEQ ID NO: 196 is an SP6 promoter site.

SEQ ID NOs: 197-199 are synthetic oligonucleotides that can bind NF-Kb.

SEQ ID NOs: 200-202 are synthetic oligonucleotides with mutated NF-Kb binding sites.

SEQ ID NOs: 203-205 are synthetic oligonucleotides that can bind estrogen receptor.

SEQ ID NOs: 206-208 are synthetic oligonucleotides with mutant estrogen receptor binding sites.

SEQ ID NOs: 209-211 are synthetic oligonucleotides that can bind SP1

SEQ ID NOs: 212-214 are synthetic oligonucleotides with mutant SP1 binding sites.

DETAILED DESCRIPTION

I. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

To facilitate review of the various embodiments of this disclosure, the following explanations of specific terms are provided:

Amplifying a Nucleic Acid Molecule:

to increase the number of copies of a nucleic acid molecule, such as a double stranded synthetic oligonucleotide described herein. The resulting products are called amplification products. An example of in vitro amplification is the polymerase chain reaction (PCR). Other examples of in vitro amplification techniques include quantitative real-time PCR, strand displacement amplification (see U.S. Pat. No. 5,744, 311); transcription-free isothermal amplification (see U.S. Pat. No. 6,033,881); repair chain reaction amplification (see WO90/01069); ligase chain reaction amplification (see EP application 320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Amplification of a nucleic acid molecule may also include the production of RNA molecules from a DNA template through a transcription reaction (such as an in vitro transcription reaction). In this case, a sequence to be amplified comprises an RNA polymerase promoter that binds to an RNA polymerase which, in the presence of ribonucleotides, produces multiple copies of an RNA sequence.

Amplification of a nucleic acid sequence may be used for any of a number of purposes, including increasing the amount of a rare sequence to be analyzed by other methods. It may also be used to identify a sequence directly (for example, though an amplification refractory mutation system) or as part of a DNA sequencing method.

Array:

An arrangement of molecules, such as biological macromolecules (such as peptides, antibodies, or nucleic acid molecules) or biological samples (such as tissue sections), in addressable locations on or in a solid support or substrate. A "microarray" is an array that is miniaturized so as to require or be aided by microscopic examination for evaluation or analysis. Arrays are sometimes called chips or biochips. The array of molecules ("features") makes it possible to carry out a large number of analyses on a sample at one time. In certain example arrays, one or more molecules (such as an oligonucleotide probe) will occur on the array a plurality of times (such as two or three times), for instance to provide internal controls. The number of addressable locations on the array can vary, for example from at least one, to at least 2, to at least 5, to at least 10, at least 20, at least 30, at least 50, at least 75, at least 100, at least 150, at least 200, at least 300, at least 500, least 550, at least 600, at least 800, at least 1000, at least 10,000, at least 100,000, or more. In particular examples, an array includes nucleic acid molecules, such as oligonucleotide sequences that are at least 10 nucleotides in length.

In particular examples, the array may comprise an oligonucleotide that can hybridize to a tag sequence on a nucleic acid probe. In further examples, the array may be a universal array that can bind a set of tags. Such an array might be stripped and reused as appropriate (see US Patent Application Publication Number 2009/0061424 which is incorporated by reference herein.)

Within an array, each arrayed biomolecule is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Binding or Stable Binding:

Physical methods of detecting the binding of complementary strands of nucleic acid molecules, include but are not limited to, such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is an increase in absorption at a characteristic temperature as the oligonucleotide (or analog) and target disassociate from each other, or melt. In another example, the method involves detecting a signal, such as a detectable label, present on one or both nucleic acid molecules. The binding between an oligomer and its target nucleic acid is frequently characterized by the temperature ($T_m$) at which 50% of the oligomer is melted from its target. A higher $T_m$ indicates a stronger or more stable complex relative to a complex with a lower $T_m$.

Buffer Solution:

An aqueous solution consisting of a mixture of a weak acid and its conjugate base or a weak base and its conjugate acid. It has the property that the pH of the solution changes very little when a small amount of acid or base is added to it. Buffer solutions can keep pH at a nearly constant value in a wide variety of chemical applications.

Contacting:

Placement in direct physical association; includes solid, liquid, and gaseous associations. Contacting includes contact between one molecule and another molecule. Contacting can occur in vitro with isolated cells or tissue or in vivo by administering to a subject. The concept of contacting may also be encompassed by adding a molecule to a solid, liquid, or gaseous mixture.

Control:

A control may be any sample or standard used for comparison with an experimental sample. In some examples, the control is a sample obtained from a healthy patient or a non-tumor tissue sample obtained from a patient diagnosed with cancer (such as non-tumor tissue adjacent to the tumor). In some examples, the control is a historical control or standard reference value or range of values (such as a previously tested control sample, such as a group of cancer patients with poor prognosis, or group of samples that represent baseline or normal values, such as the level of one or more of the genes disclosed herein in non-tumor tissue). A control may also serve as a threshold level of expression of a biomarker that indicates a particular disease outcome.

Electrophoresis:

The process of separating a mixture of charged molecules based on the different mobility of these charged molecules in response to an applied electric current. A particular type of electrophoresis is gel electrophoresis. The mobility of a molecule is generally related to the characteristics of the charged molecule, such as size, shape, and surface charge amongst others. The mobility of a molecule also is influenced by the electrophoretic medium, for example the composition of the electrophoresis gel. For example, when the electrophoretic medium is cross-linked acrylamide (polyacrylamide) increasing the percentage if acrylamide in the gel reduces the size of the resulting pores in the gel and retards the mobility of a molecule relative to a gel with a lower percentage of acrylamide (larger pore size). Gel electrophoresis can be performed for analytical purposes, but can be used as a preparative technique to partially purify molecules prior to use of other methods, such as mass spectrometry, PCR, cloning, DNA sequencing, array analysis, and immuno-blotting.

Label:

A detectable compound or composition that is conjugated directly or indirectly to another molecule (such as an oligonucleotide) to facilitate detection of that molecule. Specific, non-limiting examples of labels include fluorescent molecules, enzymatic linkages and radioactive isotopes.

Nucleic Acid Molecules:

A deoxyribonucleotide or ribonucleotide polymer including, without limitation, cDNA, mRNA, genomic DNA, methylated DNA, and synthetic (such as chemically synthesized) nucleic acids such as DNA, RNA, and/or methylated oligonucleotides. The nucleic acid molecule can be double-stranded or single-stranded. Where single-stranded, the nucleic acid molecule can be the sense strand or the anti-sense strand. In addition, nucleic acid molecule can be circular or linear. A nucleic acid molecule may also be termed a polynucleotide and the terms are used interchangeably.

Oligonucleotide:

A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide.

Particular oligonucleotides and oligonucleotide analogs can include linear sequences up to about 200 nucleotides in length, for example a sequence (such as DNA or RNA) that is at least 6 nucleotides, for example at least 8, at least 10, at least 15, at least 20, at least 21, at least 25, at least 30, at least 35, at least 40, at least 45, at least 50, at least 100 or even at least 200 nucleotides long, including 85-130 nucleotides long.

An oligonucleotide can be used to detect the presence of a complementary sequence by molecular hybridization. Such an oligonucleotide can also be termed a probe. In particular examples, such oligonucleotides include a label that permits detection of oligonucleotide probe:target sequence hybridization complexes. In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

An oligonucleotide can be used to prime a nucleic acid amplification. Such an oligonucleotide may also be termed a primer. An oligonucleotide primer can be annealed to a complementary target nucleic acid molecule by nucleic acid hybridization to form a hybrid between the primer and the target nucleic acid strand. A primer can be extended along the target nucleic acid molecule by a polymerase enzyme.

The specificity of an oligonucleotide primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50, 85, 100, or 120 or more consecutive nucleotides. In particular examples, a primer is at least 15 nucleotides in length, such as at least 15 contiguous nucleotides complementary to a target nucleic acid molecule.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction.

Nucleic acid probes and/or primers can be readily prepared based on the nucleic acid molecules provided herein. PCR primer pairs and probes can be derived from a known sequence for example, by using any of a number of computer programs intended for that purpose such as Primer (Version 0.5, © 1991, Whitehead Institute for Biomedical Research, Cambridge, Mass.) or PRIMER EXPRESS® Software (Applied Biosystems, Foster City, Calif.).

Methods for preparing and using oligonucleotide and other nucleic acid probes and primers and methods for labeling and guidance in the choice of labels appropriate for various purposes are described, for example, in Sambrook et al (In Molecular Cloning: A Laboratory Manual, CSHL, New York, 1989), Ausubel et al (ed.) (In Current Protocols in Molecular Biology, John Wiley & Sons, New York, 1998), and Innis et al (PCR Protocols, A Guide to Methods and Applications, Academic Press, Inc., San Diego, Calif., 1990).

Promoter:

An array of nucleic acid control sequences, which directs transcription of a nucleic acid. Typically, a eukaryotic a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription, such as specific DNA sequences that are recognized by proteins known as transcription factors.

In prokaryotes, a promoter is recognized by RNA polymerase and an associated sigma factor, which in turn are brought to the promoter DNA by an activator protein binding to its own DNA sequence nearby.

Sample (or Biological Sample):

A specimen containing genomic DNA, RNA (including mRNA), protein, or combinations thereof, obtained from a subject. As used herein, biological samples include cells, tissues, and bodily fluids, such as: blood; derivatives and fractions of blood, such as plasma or serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In a particular example, a sample includes a tumor biopsy (such as a prostate tumor biopsy). In another example, a sample includes circulating tumor cells, such as tumor cells present in blood of a subject with a tumor.

Obtaining a biological sample includes, but need not be limited to any method of collecting a particular sample known in the art. Obtaining a biological sample from a subject also encompasses receiving a sample that was collected at a different location than where a method is performed; receiving a sample that was collected by a different individual than an individual that performs the method, receiving a sample that was collected at any time period prior to the performance of the method, receiving a sample that was collected using a different instrument than the instrument that performs the method, or any combination of these. Obtaining a biological sample from a subject also encompasses situations in which the collection of the sample and performance of the method are performed at the same location, by the same individual, at the same time, using the same instrument, or any combination of these.

A biological sample encompasses any fraction of a biological sample or any component of a biological sample that may be isolated and/or purified from the biological sample. For example: when cells are isolated from blood or tissue, including specific cell types sorted on the basis of biomarker expression; or when nucleic acid or protein is purified from a fluid or tissue; or when blood is separated into fractions such as plasma, serum, buffy coat PBMC's or other cellular and non-cellular fractions on the basis of centrifugation and/or filtration. A biological sample further encompasses biological samples or fractions or components thereof that have undergone a transformation of mater or any other manipulation. For example, a cDNA molecule made from reverse transcription of mRNA purified from a biological sample may be termed a biological sample.

A biological sample may be obtained from any source including any organism (living, dead, or extinct) or any cells derived from an organism or any artificial cells that may comprise nucleic acids and/or nucleic acid binding proteins. Examples include animals, plants, bacteria, archea, fungi, prions, viruses, or any other source. Biological samples may also include strata that may contain nucleic acids or nucleic acid binding proteins including water, soil, air, fossilized material, including strata from both terrestrial and extraterrestrial origin.

Transcription Factor:

A protein that regulates transcription. In particular, transcription factors regulate the binding of RNA polymerase and the initiation of transcription. A transcription factor binds upstream or downstream to either enhance or repress transcription of a gene by assisting or blocking RNA polymerase binding. The term transcription factor includes both inactive and activated transcription factors.

Transcription factors are typically modular proteins that affect regulation of gene expression. Exemplary transcription factors include AAF, ab1, ADA2, ADA-NF1, AF-1, AFP1, AhR, AIIN3, ALL-1, alpha-CBF, alpha-CP1, alpha-CP2a, alpha-CP2b, alphaHo, alphaH2-alphaH3, Alx-4, aMEF-2, AML1, AML1a, AML1b, AML1c, AML1DeltaN, AML2, AML3, AML3a, AML3b, AMY-1L, A-Myb, ANF, AP-1, AP-2alphaA, AP-2alphaB, AP-2beta, AP-2gamma, AP-3 (1), AP-3 (2), AP-4, AP-5, APC, AR, AREB6, Arnt, Arnt (774 M form), ARP-1, ATBF1-A, ATBF1-B, ATF, ATF-1, ATF-2, ATF-3, ATF-3deltaZIP, ATF-a, ATF-adelta, ATPF1, Barh11, Barh12, Barx1, Barx2, Bc1-3, BCL-6, BD73, beta-catenin, Bin1, B-Myb, BP1, BP2, brahma, BRCA1, Brn-3a, Brn-3b, Brn-4, BTEB, BTEB2, B-TFIID, C/EBPalpha, C/EBPbeta, C/EBPdelta, CACCbinding factor, Cart-1, CBF (4), CBF (5), CBP, CCAAT-binding factor, CCMT-binding factor, CCF, CCG1, CCK-1a, CCK-1b, CD28RC, cdk2, cdk9, Cdx-1, CDX2, Cdx-4, CFF, Chx1O, CLIM1, CLIM2, CNBP, CoS, COUP, CP1, CP1A, CP1C, CP2, CPBP, CPE binding protein, CREB, CREB-2, CRE-BP1, CRE-BPa, CREMalpha, CRF, Crx, CSBP-1, CTCF, CTF, CTF-1, CTF-2, CTF-3, CTF-5, CTF-7, CUP, CUTL1, Cx, cyclin A, cyclin T1, cyclin T2, cyclin T2a, cyclin T2b, DAP, DAX1, DB1, DBF4, DBP, DbpA, DbpAv, DbpB, DDB, DDB-1, DDB-2, DEF, deltaCREB, deltaMax, DF-1, DF-2, DF-3, Dlx-1, Dlx-2, Dlx-3, Dlx4 (long isoform), Dlx-4 (short isoform, Dlx-5, Dlx-6, DP-1, DP-2, DSIF, DSIF-β14, DSIF-β160, DTF, DUX1, DUX2, DUX3, DUX4, E, E12, E2F, E2F+E4, E2F+p107, E2F-1, E2F-2, E2F-3, E2F-4, E2F-5, E2F-6, E47, E4BP4, E4F, E4F1, E4TF2, EAR2, EBP-80, EC2, EF1, EF-C, EGR1, EGR2, EGR3, EIIaE-A, EIIaE-B, EIIaE-Calpha, EIIaE-Cbeta, EivF, EIf-1, Elk-1, Emx-1, Emx-2, Emx-2, En-1, En-2, ENH-bind. prot., ENKTF-1, EPAS1, epsilonF1, ER, Erg-1, Erg-2, ERR1, ERR2, ETF, Ets-1, Ets-1 deltaVi1, Ets-2, Evx-1, F2F, factor 2, Factor name, FBP, f-EBP, FKBP59, FKHL18, FKHRL1P2, Fli-1, Fos, FOXB1, FOXC1, FOXC2, FOXD1, FOXD2, FOXD3, FOXD4, FOXE1, FOXE3, FOXF1, FOXF2, FOXG1a, FOXG1b, FOXG1c, FOXH1, FOXI1, FOXJ1a, FOXJ1b, FOXJ2 (long isoform), FOXJ2 (short isoform), FOXJ3, FOXK1a, FOXK1b, FOXK1c, FOXL1, FOXM1a, FOXM1b, FOXM1c, FOXN1, FOXN2, FOXN3, FOX01a, FOX01b, FOXO2, FOXO3a, FOXO3b, FOXO4, FOXP1, FOXP3, Fra-1, Fra-2, FTF, FTS, G factor, G6 factor, GABP, GABP-alpha, GABP-beta1, GABP-beta2, GADD 153, GAF, gammaCMT, gammaCAC1, gammaCAC2, GATA-1, GATA-2, GATA-3, GATA-4, GATA-5, GATA-6, Gbx-1, Gbx-2, GCF, GCMa, GCNS, GF1, GLI, GLI3, GR alpha, GR beta, GRF-1, Gsc, Gsc1, GT-IC, GT-IIA, GT-IIBalpha, GT-IIBbeta, H1TF1, H1TF2, H2RIIBP, H4TF-1, H4TF-2, HAND1, HAND2, HB9, HDAC1, HDAC2, HDAC3, hDaxx, heat-induced factor, HEB, HEB1-p67, HEB1-p94, HEF-1 B, HEF-1T, HEF-4C, HEN1, HEN2, Hesx1, Hex, HIF-1, HIF-1alpha, HIF-1beta, HiNF-A, HiNF-B, HINF-C, HINF-D, HiNF-D3, HiNF-E, HiNF-P, HIP1, HIV-EP2, Hlf, HLTF, HLTF (Met123), HLX, HMBP, HMG I, HMG I(Y), HMG Y, HMGI-C, HNF-1A, HNF-1B, HNF-1C, HNF-3, HNF-3alpha, HNF-3beta, HNF-3gamma, HNF4, HNF-4-alpha, HNF4alpha1, HNF-4-alpha2, HNF-4-alpha3, HNF-4-alpha4, HNF4gamma, HNF-6alpha, hnRNP K, HOX11, HOXA1, HOXA10, HOXA10 PL2, HOXA11, HOXA13, HOXA2, HOXA3, HOXA4, HOXA5, HOXA6, HOXA7, HOXA9A, HOXA9B, HOXB-1, HOXB13, HOXB2, HOXB3, HOXB4, HOXB5, HOXB6, HOXA5, HOXB7, HOXB8, HOXB9, HOXC10, HOXC11, HOXC12, HOXC13, HOXC4, HOXC5, HOXC6, HOXC8, HOXC9, HOXD10, HOXD11, HOXD12, HOXD13, HOXD3, HOXD4, HOXD8, HOXD9, Hp55, Hp65, HPX42B, HrpF, HSF, HSF1 (long), HSF1 (short), HSF2, hsp56, Hsp90, IBP-1, ICER-II, ICER-ligamma, ICSBP, Id1, Id1 H', Id2, Id3, Id3/Heir-1, IF1, IgPE-1, IgPE-2, IgPE-3, IkappaB, IkappaB-alpha, IkappaB-beta, IkappaBR, II-1 RF, IL-6 RE-BP, 11-6 RF, INSAF, IPF1, IRF-1, IRF-2, ir1B, IRX2a, Irx-3, lrx-4, ISGF-1, ISGF-3, ISGF3alpha, ISGF-3gamma, lsl-1, ITF, ITF-1, ITF-2, JRF, Jun, JunB, JunD, kappay factor, KBP-1, KER1, KER-1, Kox1, KRF-1, Ku autoantigen, KUP, LBP-1, LBP-1a, LBX1, LCR-F1, LEF-1, LEF-1B, LF-A1, LHX1, LHX2, LHX3a, LHX3b, LHX5, LHX6.1a, LHX6.1b, LIT-1, Lmo1, Lmo2, LMX1A, LMX1B, L-My1 (long form), L-My1 (short form), L-My2, LSF, LXRalpha, LyF-1, LyI-1, M factor, Mad1, MASH-1, Max1, Max2, MAZ, MAZ1, MB67, MBF1, MBF2, MBF3, MBP-1 (1), MBP-2, MDBP, MEF-2, MEF-2B, MEF-2C (433 AA form), MEF-2C (465 AA form), MEF-2C (473 M form), MEF-2C/delta32 (441 AA form), MEF-2D00, MEF-2D0B, MEF-2DA0, MEF-2DA'0, MEF-2DAB, MEF-2DA'B, Meis-1, Meis-2a, Meis-2b, Meis-2c, Meis-2d, Meis-2e, Meis3, Meox1, Meox1a, Meox2, MHox (K-2), Mi, MIF-1, Miz-1, MM-1, MOP3, MR, Msx-1, Msx-2, MTB-Zf, MTF-1, mtTF1, Mxi1, Myb, Myc, Myc 1, Myf-3, Myf-4, Myf-5, Myf-6, MyoD, MZF-1, NC1, NC2, NCX, NELF, NER1, Net, NF III-a, NF III-c, NF III-e, NF-1, NF-1A, NF-1B, NF-1X, NF-4FA, NF-4FB, NF-4FC, NF-A, NF-AB, NFAT-1, NF-AT3, NF-Atc, NF-Atp, NF-Atx, NfbetaA, NF-CLE0a, NF-CLE0b, NFdeltaE3A, NFdeltaE3B, NFdeltaE3C, NFdeltaE4A, NFdeltaE4B, NFdeltaE4C, Nfe, NF-E, NF-E2, NF-E2 p45, NF-E3, NFE-6, NF-Gma, NF-GMb, NF-IL-2A, NF-IL-2B, NF-jun, NF-kappaB, NF-kappaB(-like), NF-kappaB1, NF-kappaB1, precursor, NF-kappaB2, NF-kappaB2 (p49), NF-kappaB2 precursor, NF-kappaE1, NF-kappaE2, NF-kappaE3, NF-MHCIIA, NF-MHCIIB, NF-muE1, NF-muE2, NF-muE3, NF-S, NF-X, NF-X1, NF-X2, NF-X3, NF-Xc, NF-YA, NF-Zc, NF-Zz, NHP-1, NHP-2, NHP3, NHP4, NKX2-5, NKX2B, NKX2C, NKX2G, NKX3A, NKX3A v1, NKX3A v2, NKX3A v3, NKX3A v4, NKX3B, NKX6A, Nmi, N-Myc, N-Oct-2alpha, N-Oct-2beta, N-Oct-3, N-Oct-4, N-Oct-5a, N-Oct-Sb, NP-TCII, NR2E3, NR4A2, Nrf1, Nrf-1, Nrf2, NRF-2beta1, NRF-2gamma1, NRL, NRSF form 1, NRSF form 2, NTF, O2, OCA-B, Oct-1, Oct-2, Oct-2.1, Oct-2B, Oct-2C, Oct-4A, Oct4B, Oct-5, Oct-6, Octa-factor, octamer-binding factor, oct-B2, oct-B3, Otx1, Otx2, OZF, p107, p130, p28 modulator, p300, p38erg, p45, p49erg, -p53, p55, p55erg, p65delta, p67, Pax-1, Pax-2, Pax-3, Pax-3A, Pax-3B, Pax-4, Pax-5, Pax-6, Pax-6/Pd-5a, Pax-7, Pax-8, Pax-8a, Pax-8b, Pax-8c, Pax-8d, Pax-8e, Pax-8f, Pax-9, Pbx-1a, Pbx-1b, Pbx-2, Pbx-3a, Pbx-3b, PC2, PC4, PC5, PEA3, PEBP2alpha, PEBP2beta, Pit-1, PITX1, PITX2, PITX3, PKNOX1, PLZF, PO-B, Pontin52, PPARalpha, PPARbeta, PPARgamma1, PPARgamma2, PPUR, PR, PR A, pRb, PRD1-BF1, PRDI-BFc, Prop-1, PSE1, P-TEFb, PTF, PTFalpha, PTFbeta, PTFdelta, PTFgamma, Pu box binding factor, Pu box binding factor (BJA-B), PU.1, PuF, Pur factor, R1, R2, RAR-alpha1, RAR-beta, RAR-beta2, RAR-gamma, RAR-gamma1, RBP60, RBP-Jkappa, Rel, RelA, RelB, RFX, RFX1, RFX2, RFX3, RFX5, RF-Y, RORalpha1, RORalpha2, RORalpha3, RORbeta, RORgamma, Rox, RPF1, RPGalpha, RREB-1, RSRFC4, RSRFC9, RVF, RXR-alpha, RXR-beta, SAP-1a, SAP1b, SF-1, SHOX2a, SHOX2b, SHOXa, SHOXb, SHP, SIII-p110, SIII-p15, SIII-p18, SIM1, Six-1, Six-2, Six-3, Six-4, Six-5, Six-6, SMAD-1, SMAD-2, SMAD-3, SMAD-4, SMAD-5, SOX-11, SOX-12, Sox-4, Sox-5, SOX-9, Sp1, Sp2, Sp3, Sp4, Sph factor, Spi-B, SPIN, SRCAP, SREBP-1a, SREBP-1b, SREBP-1c, SREBP-2, SRE-ZBP, SRF, SRY, SRP1, Staf-50, STAT1alpha, STAT1beta, STAT2, STAT3, STAT4, STATE, T3R, T3R-alpha1, T3R-alpha2, T3R-beta, TAF(I)110, TAF (I)48, TAF(I)63, TAF(II)100, TAF(II)125, TAF(II)135, TAF (II)170, TAF(II)18, TAF(II)20, TAF(II)250, TAF(II) 250Delta, TAF(II)28, TAF(II)30, TAF(II)31, TAF(II)55, TAF(II)70-alpha, TAF(II)70-beta, TAF(II)70-gamma, TAF-I, TAF-II, TAF-L, Ta1-1, Ta1-1beta, Ta1-2, TAR factor, TBP, TBX1A, TBX1 B, TBX2, TBX4, TBX5 (long isoform), TBX5 (short isoform), TCF, TCF-1, TCF-1A, TCF-1B, TCF-1C, TCF-1D, TCF-1E, TCF-1F, TCF-1G, TCF-2alpha, TCF-3, TCF-4, TCF-4(K), TCF-4B, TCF-4E, TCFbeta1, TEF-1, TEF-2, te1, TFE3, TFEB, TFIIA, TFIIA-alpha/beta precursor, TFIIA-alpha/beta precursor, TFIIA-gamma, TFIIB, TFIID, TFIIE, TFIIE-alpha, TFIIE-beta, TFIIF, TFIIF-alpha, TFIIF-beta, TFIIH, TFIIH*, TFIIH-CAK, TFIIH-cyclin H, TFIIH-ERCC2/CAK, TFIIH-MAT1, TFIIH-MO15, TFIIH-p34, TFIIH-p44, TFIIH-p62, TFIIH-p80, TFIIH-p90, TFII-I, Tf-LF1, Tf-LF2, TGIF, TGIF2, TGT3, THRA1, TIF2, TLE1, TLX3, TMF, TR2, TR2-11, TR2-9, TR3, TR4, TRAP, TREB-1, TREB-2, TREB-3, TREF1, TREF2, TRF (2), TTF-1, TXRE BP, TxREF, UBF, UBP-1, UEF-1, UEF-2, UEF-3, UEF-4, USF1, USF2, USF2b, Vav, Vax-2, VDR, vHNF-1A, vHNF-1B, vHNF-1C, VITF, WSTF, WT1, WT1I, WT1 I-KTS, WT1 I-del2, WT1-KTS, WT1-del2, X2BP, XBP-1, XW-V, XX, YAF2, YB-1, YEBP, YY1, ZEB, ZF1, ZF2, ZFX, ZHX1, ZIC2, ZID, ZNF174, amongst others.

An activated transcription factor is a transcription factor that has been activated by a stimulus resulting in a measurable change in the state of the transcription factor, for example a post-translational modification, such as phosphorylation, methylation, and the like. Activation of a transcription factor can result in a change in the affinity for a particular DNA sequence or of a particular protein, such as another transcription factor and/or cofactor.

II. Detailed Description of Several Embodiments a. Synthetic Oligonucleotides

Disclosed herein are synthetic oligonucleotides useful in the detection of DNA binding proteins. The oligonucleotides comprise (a) a sequence that includes a nucleic acid binding protein binding site, (b) a sequence that facilitates the amplification of the primer such as a binding site for a PCR primer and/or an RNA polymerase promoter, and (c) a tag sequence. In some examples, the nucleic acid binding protein binding site is 20 nucleotides in length. At least the nucleic acid binding protein binding site is double stranded and the entire synthetic oligonucleotide can be double stranded. In still further examples, the oligonucleotide comprises SEQ ID NO: 195, SEQ ID NO: 196, and/or SEQ ID NOs: 3-98.

The nucleic acid binding protein binding site may be any binding site for a protein that can bind a specific nucleic acid sequence. Such binding sites include known binding sites, putative binding sites, mutant or otherwise altered binding sites, or even random sets of nucleotides that are used to seek out unknown nucleic acid binding proteins. In addition, the nucleic acid binding site may comprise methylated or otherwise altered nucleic acids.

A tag sequence is an artificial nucleic acid sequence that does not bind any known nucleic acid binding protein. In some examples, a tag sequence is a non-naturally occurring nucleic acid sequence that does not bind any known nucleic acid binding protein. One of skill in the art in light of this disclosure will understand how to make a tag sequence or set of tag sequences that can be incorporated into the probes described herein. Additionally, one of skill in the art in light of this disclosure would be able to determine without undue experimentation whether or not a particular sequence binds to a nucleic acid binding protein and would therefore not use that sequence as a tag sequence. Examples of tag sequences include SEQ ID NOs: 3-98 herein.

In some examples the oligonucleotide probe is between 85 and 130 nucleotides in length, between, 88 and 120 nucleotides, between 90 and 110 nucleotides, between 88 and 98 nucleotides in length, between 90 and 96 nucleotides in length, between 92 and 94 nucleotides in length, including 85, 86, 87, 88, 89, 90, 91, 92, 93, 94, 95, 96, 97, 98, 100, 101, 102, 103, 104, 105, 106, 107, 018, 019, 110, 111, 112, 113, 114, 115, 116, 117, 118, 119, 120, 121, 122, 123, 124, 125, 126, 127, 128, 129, or 130 nucleotides in length. An exemplary set of the synthetic oligonucleotides described herein includes SEQ ID NOs: 99-194 and SEQ ID NOs: 197-214 herein.

In some examples, oligonucleotides described herein contain one or more modifications. Modified oligonucleotides include those comprising modified backbones or non-natural internucleoside linkages. As defined herein, oligonucleotides having modified backbones include those that retain a phosphorus atom in the backbone and those that do not have a phosphorus atom in the backbone.

Examples of modified oligonucleotide backbones include, but are not limited to, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of the nucleoside units are linked 3'-5' to 5'-3' or 2'-5' to 5'-2'. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides can also contain one or more substituted sugar moieties. In some examples, the oligonucleotides can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Oligonucleotides can also have sugar mimetics such as cyclobutyl moieties in place of the pentofuranosyl sugar. Representative United States patents that teach the preparation of modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Oligonucleotides can also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further modified bases have been described (see, for example, U.S. Pat. No. 3,687,808; and Sanghvi, Y. S., Chapter 15, Antisense Research and Applications, pages 289-302, Crooke, S. T. and Lebleu, B., ed., CRC Press, 1993).

Certain of these modified bases are useful for increasing the binding affinity. For example, 5-methylcytosine substitutions have been shown to increase nucleic acid duplex stability by 0.6-1.2° C. Representative U.S. patents that teach the preparation of modified bases include, but are not limited to, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692, each of which is herein incorporated by reference.

Also disclosed is a synthetic oligonucleotide library that includes a plurality of the synthetic oligonucleotides described herein. The library can contain at least, 2, 16, 48, 96, 384, 1000, 10,000, or 100,000 or more different probes. Each synthetic oligonucleotide in the library can have a different nucleic acid binding protein binding site. Each probe can comprise a different nucleic acid protein binding site than all the other probes in the library. Additionally, each synthetic oligonucleotide in the library can comprise a different tag sequence than all the other tag sequences with each tag sequence in the library coupled with a particular nucleic acid protein binding site.

b. Oligonucleotide Synthesis

The synthetic oligonucleotides disclosed herein may be synthesized by any method now known in the art or yet to be disclosed. Oligonucleotide synthesis may be carried out by the addition of nucleotide residues to the 5'-terminus of a growing chain. Elements of oligonucleotide synthesis include: de-blocking (detritylation): A DMT group is removed with a solution of an acid, such as TCA or Dichloroacetic acid (DCA), in an inert solvent (dichloromethane or toluene) and washed out, resulting in a free 5' hydroxyl group on the first base. Coupling: A nucleoside phosphoramidite (or a mixture of several phosphoramidites)

is activated by an acidic azole catalyst, tetrazole, 2-ethylthiotetrazole, 2-bezylthiotetrazole, 4,5-dicyanoimidazole, or a number of similar compounds. This mixture is brought in contact with the starting solid support (first coupling) or oligonucleotide precursor (following couplings) whose 5'-hydroxy group reacts with the activated phosphoramidite moiety of the incoming nucleoside phosphoramidite to form a phosphite triester linkage. The phosphoramidite coupling may be carried out in anhydrous acetonitrile. Unbound reagents and by-products may be removed by washing.

A small percentage of the solid support-bound 5'-OH groups (0.1 to 1%) remain unreacted and should be permanently blocked from further chain elongation to prevent the formation of oligonucleotides with an internal base deletion commonly referred to as (n−1) shortmers. This is done by acetylation of the unreacted 5'-hydroxy groups using a mixture of acetic anhydride and 1-methylimidazole as a catalyst. Excess reagents are removed by washing.

The newly formed tricoordinated phosphite triester linkage is of limited stability under the conditions of oligonucleotide synthesis. The treatment of the support-bound material with iodine and water in the presence of a weak base (pyridine, lutidine, or collidine) oxidizes the phosphite triester into a tetracoordinated phosphate triester, a protected precursor of the naturally occurring phosphate diester internucleosidic linkage. This step can be substituted with a sulfurization step to obtain oligonucleotide phosphorothioates. In the latter case, the sulfurization step is carried out prior to capping. Upon the completion of the chain assembly, the product may be released from the solid phase to solution, deprotected, and collected. Products may be isolated by HPLC to obtain the desired oligonucleotides in high purity.

c. Oligonucleotide Labeling

The hybridized synthetic oligonucleotides can be detected by detecting one or more labels bonded to the sample nucleic acids. The labels can be incorporated by any of a number of methods. In one example, the label is simultaneously incorporated during nucleic acid amplification. Thus, for example, polymerase chain reaction (PCR) with labeled primers or labeled nucleotides will provide a labeled amplification product. Alternatively, transcription amplification using an RNA polymerase and a labeled nucleotide (such as fluorescein-labeled UTP and/or CTP) can be used to incorporate a label into the transcribed nucleic acids.

Alternatively, a label may be added directly to the original nucleic acid sample (such as mRNA, polyA mRNA, cDNA, etc.) or to the amplification product after the amplification is completed. Methods of attaching labels to nucleic acids are well known to those of skill in the art and include, for example, nick translation or end-labeling (e.g. with a labeled RNA) by phosphorylation of the nucleic acid and subsequent attachment (ligation) of a nucleic acid linker joining the sample nucleic acid to a label (e.g., a fluorophore).

Detectable labels suitable for use include any composition detectable by spectroscopic, photochemical, biochemical, immunochemical, electrical, optical, chemical, or other detection systems. Useful labels include biotin for staining with labeled streptavidin conjugate, magnetic beads (for example DYNABEADS™), fluorescent dyes (for example, fluorescein, Texas red, rhodamine, green fluorescent protein, and the like), radiolabels (for example, 3H, 125I, 35S, 14C, or 32P), enzymes (for example, horseradish peroxidase, alkaline phosphatase and others commonly used in an ELISA), and colorimetric labels such as colloidal gold or colored glass or plastic (for example, polystyrene, polypropylene, latex, etc.) beads. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149; and U.S. Pat. No. 4,366,241.

Methods of detecting such labels are also well known. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and fluorescent and colorimetric labels are detected by visualizing the colored label.

The label may be added to the synthetic oligonucleotide prior to, or after amplification and/or hybridization to the array. Some detectable labels are directly attached to or incorporated into the synthetic oligonucleotide prior to hybridization. Other labels are joined to the synthetic oligonucleotide after hybridization to the array. Often, the indirect label is attached to a binding moiety that has been attached to the target nucleic acid prior to the hybridization. Thus, for example, the target nucleic acid can be biotinylated before the hybridization. After hybridization, an avidin-conjugated fluorophore can bind the biotin hybrid duplexes comprising the biotin, thereby providing a label that is easily detected (see Laboratory Techniques in Biochemistry and Molecular Biology, Vol. 24: Hybridization With Nucleic Acid Probes, P. Tijssen, ed. Elsevier, N.Y., 1993).

d. Kits

Also disclosed is a kit comprising the synthetic oligonucleotide library that comprises the synthetic oligonucleotides disclosed herein and an array that comprises at least 2, 16, 48, 96, 384, 1000, 10,000 or 100,000 bound synthetic oligonucleotides with the bound synthetic oligonucleotides bound to a solid substrate. Each bound synthetic oligonucleotide comprises a sequence that is complementary (binds via Watson-Crick base pairing—A-T, C-G) to the tag sequence on one of the synthetic oligonucleotides in the library. The bound synthetic oligonucleotides are addressable within the context of the microarray such that a known synthetic oligonucleotide can bind to a bound oligonucleotide comprising the complement to its tag sequence in a known location on the array. Detection of the binding of the synthetic oligonucleotide to an addressed position on the array further can identify the nucleic acid binding protein binding site and, in turn indicate that the nucleic acid binding protein was originally present in a sample. Examples of complements to tag sequences in the bound synthetic oligonucleotides are the complementary sequences of SEQ ID NOs: 3-98.

e. Methods of Use

Also disclosed is a method of detecting the presence of a DNA binding protein in a sample. This method comprises, contacting a library of synthetic oligonucleotides described herein with a sample that may contain a nucleic acid binding protein. The synthetic oligonucleotides are allowed to bind to the nucleic acid binding protein thereby forming complexes. The complexes are purified by electrophoresis and a label is incorporated into the synthetic oligonucleotide. The synthetic oligonucleotide is hybridized to an array comprising bound synthetic oligonucleotides as described above and the presence of the label is detected on the array. Detection of the label on a specific address on the array is an indication that a nucleic acid binding protein that can specifically bind the nucleic acid binding site on the synthetic oligonucleotide that is addressed to the specific address on the array via its tag sequence was originally present in the sample.

The label may be any label including a fluorescent label. Incorporation of the label may be by any method including any method that amplifies or transcribes the nucleic acid such as by performing PCR amplification or contacting the complex with an RNA polymerase. The electrophoresis may be any type of electrophoresis including electrophoresis performed using the method and device described in US Patent Application Publication number 2012/0160683 (which is incorporated by reference herein in its entirety.)

For example, the disclosed oligonucleotides may be used with electrophoresis which utilizes a cassette comprising a proximal end and a distal end opposite the proximal end, a front face and a back face substantially parallel to the front face, and at least one chamber defined between the front face and the back face, the chamber having an upper portion and a lower portion, wherein the upper portion includes an upper opening at or near the proximal end of the cassette and the lower portion includes a lower opening at or near the distal end of the cassette, and wherein the front face comprises at least one window opening into the upper portion of the chamber. In some embodiments, the cassette can further comprise a semi-permeable membrane covering at least a portion of the at least one window opening. The semi-permeable membrane can be removably secured to the front face of the cassette. The semi-permeable membrane can be configured to allow passage of a buffer solution surrounding at least a portion of the cassette, and to at least partially block passage of a biomolecule contained within the upper portion of the at least one chamber. In some embodiments, a semi-permeable membrane can substantially block passage of a biomolecule of interest, thus substantially preventing it from exiting the chamber through the window opening. Some embodiments may utilize a cassette comprising acrylic. Some embodiments of a cassette comprise a unitary body. Cassettes can be integrated with one or more other components to form an electrophoresis device.

One embodiment of an electrophoresis device which can be utilized in the disclosed methods with the disclosed oligonucleotides comprises a cassette, wherein the cassette comprises a proximal end and a distal end opposite the proximal end, a front face and a back face substantially parallel to the front face, and at least one chamber defined between the front face and the back face, the chamber having an upper portion and a lower portion, wherein the upper portion includes an upper opening at or near the proximal end of the cassette and the lower portion includes a lower opening at or near the distal end of the cassette, and wherein the front face comprises at least one window opening into the upper portion of the chamber. The electrophoresis device can further comprise a first buffer solution in fluid contact with the lower opening of the lower portion, a second buffer solution in fluid contact with the window opening of the upper portion, and at least one electrode electrically coupled to each of the first and second buffer solutions. Fluid contact can include both direct and indirect fluid contact. For example, fluid contact can include fluid contact through a membrane, such as a semi-permeable membrane.

In some embodiments of an electrophoresis device, the cassette further comprises a semi-permeable membrane covering at least a portion of the window opening of the upper portion, such as a membrane comprising cellulose or cellophane. In one particular embodiment, the electrophoresis device, comprises a first buffer container; and a cassette capable of being coupled to the first buffer container to form a first sidewall of the first buffer container, wherein the cassette comprises a proximal end and a distal end opposite the proximal end, a front face and a back face and at least one chamber defined between the front face and the back face, the chamber having an upper portion and a lower portion, wherein the upper portion includes a proximal opening at or near the proximal end of the cassette and the lower portion includes a distal opening at or near the distal end of the cassette wherein the proximal opening and distal opening are aligned to form a straight passageway there through, and wherein the front face comprises at least one window opening into the upper portion of the chamber.

The disclosed oligonucleotides can be used with reversible current electrophoresis, such that when current is run in a first direction, free molecules elute into the buffer at the distal end of the device. Then the cassette body can be placed into a new bath, the current reversed, and the biomolecules of interest can then move in the opposite direction, out of the gel, and back into the buffer solution at the proximal end of the cassette body, where they can then be easily collected from the device.

For example, one method of separating a biomolecule of interest from a sample comprises providing a sample, wherein the sample contains a biomolecule of interest and free probes, loading the sample onto a gel in a lower portion of a cassette body, electrophoresing the sample by applying a current for a time period sufficient for substantially all of the free probes (such as one or more of the disclosed oligonucleotides) to elute out of a distal end of the lower portion, into a first buffer solution in a first buffer container, leaving the biomolecule of interest within the gel, removing the first buffer solution, providing a new buffer solution in fluid contact with the lower portion of the cassette, reversing the current with respect to the gel, and electrophoresing the sample for a time period sufficient for substantially all of the biomolecule of interest to elute out of a proximal end of the lower portion, into an upper portion of the cassette body.

Disclosed methods can further comprise collecting biomolecule of interest. Collecting the biomolecule of interest can comprise withdrawing a volume of buffer solution containing the biomolecule of interest from the upper portion of the cassette body. Collecting the biomolecule of interest can comprise securing a semi-permeable membrane over at least part of the upper portion, so as to prevent substantially all of the biomolecule of interest from passing through the semi-permeable membrane into a second buffer solution in fluid contact with the upper portion of the cassette.

In some methods, reversing the current with respect to the gel comprises switching the polarity of a first and second electrode in electrical contact with the first and second buffer solutions, respectively. In some methods, reversing the current with respect to the gel comprises changing the orientation of the gel with respect to a first and second electrode in electrical contact with the first and second buffer solutions, respectively.

Removing the first buffer solution can comprise draining the first buffer solution from a buffer container. Providing a new buffer solution in fluid contact with the lower portion of the cassette can comprise refilling the buffer container with the new buffer solution. In other methods, removing the first buffer solution comprises removing the cassette from a first buffer container containing the first buffer solution, and providing a new buffer solution in fluid contact with the lower portion of the cassette comprises placing the cassette in a second buffer container containing the new buffer solution.

EXAMPLES

The following examples are illustrative of disclosed methods. In light of this disclosure, those of skill in the art will recognize that variations of these examples and other examples of the disclosed method would be possible without undue experimentation.

Example 1

Sample Preparation

Nuclear protein extracts were prepared according to the QIAGEN® protocol using a Qproteome Nuclear Protein Kit (Catalog number 37582, QIAGEN®, Valencia, Calif.) from 20 to 25 mg tissue or 10 million cells as appropriate. The nuclear protein extracts were aliquotted in 5 µg volumes and stored at −80° C. prior to the reaction.

A blocking reaction was then performed. The blocking reaction included Poly(dI-dC) a double stranded alternating copolymer that is commonly used as a blocking agent in EMSA assays at a concentration of 1 µg/ml per 1 µg/ml of nuclear protein as well as a mixture of polynucleotides consisting of equal proportions of SEQ ID NOs 3-98. This mixture was added at 0.4 µg/ml per 1 µg/ml of nuclear protein. Exact concentrations and volumes used are as follows:

| | |
|---|---|
| Nuclear protein [1.0 µg/µl] | 5 µl |
| Poly(IC) [0.5 µg/µl] | 2 µl |
| Probe mix [200 ng/µl] | 2 µl |
| Add water to | 15 µl |

The blocking reaction lasted for 15 minutes at room temperature.

The blocked reaction mixture was then mixed with a set of oligonucleotide probes consisting of polynucleotides of SEQ ID NOs: 197-214 in the following mixture:

| | |
|---|---|
| 10x buffer | 3.0 µl |
| 50% glycerol | 1.5 µl |
| 25 mM DTT/2.5% Tween ®-20 | 3.0 µl |
| Probe set (38 ng/µl) | 1.5 µl |
| Water | 6.0 µl |

This mixture was incubated for 25 minutes at room temperature.

Probes were then run on a gel electrophoresis system configured to separate and collect complexes comprising transcription factor and bound probe from free probe. This system is described in US Patent Application 2012/0160683, which is incorporated by reference herein.

A 6% acrylamide gel was prepared as follows:

| | |
|---|---|
| 30% acrylamide | 4 ml |
| 7.5x TBE | 1.33 ml |
| Water | 14.6 ml |
| 10% APS | 100 µl |
| TEMED | 10 µl |

The running buffer was a 0.5×Tris/borate/EDTA (TBE) buffer.

The gel was run for 135 minutes, a time previously determined to be sufficient to clear all unbound probe out of the distal end of the gel. The gel cassette was rinsed, a semipermeable membrane installed in the collection chamber as described in the referenced patent application, and fresh TBE buffer added. At this point, the electrode polarity is reversed and the gel run with electrode polarity reversed for 210 minutes. After the 210 minute electrophoresis, the transcription factor protein/probe complexes are collected in about a 1.5 ml volume. The 1.5 ml volume is concentrated to 50 µl using an Amicon 10 k filter unit and the samples then purified using a QIAamp nucleotide removal kit. The volume of the eluate with the purified probes is 50 µl.

Amplification and labeling was performed using a T7 High Yield RNA® Synthesis Kit (New England Biolabs). Biotinylated UTP is added to the ribonucleotide solution from the kit to a level where the biotinylated UTP makes up 33% of the UTP in the solution. The amplification and labeling mixture is as follows:

| | |
|---|---|
| 10x buffer (from kit) | 2 µl |
| Ribonucleotide mix | 7.5 µl |
| (100 mM each ATP, CTP, GTP, 50 mM UTP and 25 mM biotinylated UTP) | |
| Purified probes from electrophoresis | 6.0 µl |
| T7 RNA polymerase (from kit) | 2.0 µl |
| Water | 2.5 µl |

Amplification/labeling was performed for 2 hours at 37° C., following which the samples are placed on ice.

Labeled RNA was purified using a QIAGEN® RNeasy Mini-elute Cleanup kit.

Microarray slides were prepared by Microarrays Inc (Huntsville, Ala.). Four subarrays of 25 nucleotide-long tag sequences were printed per slide. Complements of ninety-six tag sequences (SEQ ID NOs: 3-98) were used for each subarray. Each tag sequence was printed 4 times—once in each subarray.

Labeled RNA was mixed with hybridization buffers A and B (Hyb & Frag Buffers, CodeLink®, Applied Microarrays) and hybridized to each microarray under the following conditions:

Samples were heated at 68° C. for 3 minutes and then placed on ice for 2 minutes. Then 55 µl of sample was injected into a Tecan 400 pro hybridization station at 37° C. for 18 hours. Samples were washed with 0.75 TNT fast wash at room temperature, 2 times, then incubated in 0.75 TNT at 37° C. for 1 hour.

A Cy5-Streptavidin working solution was prepared by mixing 1 µCy5 with 499 µl TNB buffer. A 55 µl volume of Cy5-Streptavidin working solution was injected into the sample through a positive pressure pipette and incubate at room temperature for 30 min. Slides were then washed with 1×TNT wash 4 times at 5 minutes per wash. Slides were then washed with 0.1×SSC/0.05% Tween 20 at room temperature for 30 seconds. Slides were then dried by nitrogen flow.

A GenePix 4000B Microarray scanner was used to scan the slide using a single wavelength scan at 635 nm. The PMT gain ranged from 450-650.

Normalization of signal was performed as follows:

Average signal of the subarray=total signal of the subarray/(96×4)

Average signal of the probe=total signal of the probe/4

Relative strength of a probe=Average signal of the probe/Average signal of the subarray

Example 2

Quantifiable Detection of NF-κB in Liver Cells

Liver nuclear extract was used as the control (group 1), 10 ng (group 2), 50 ng (group 3) and 100 ng (group 4) of purified NF-Kb protein were added to same amount of liver nuclear extract and then bind to a group of mixed probes, which included NF-Kb probes, ER-alpha probes, SP-1 probes, mutated NF-Kb probes, mutated ER-alpha probes, and mutated SP-1 probes. The probes that bind to nuclear protein in the samples were separated with our gel device and then labeled and hybridized to individual subarray of microarray slide. The relative strength of one probes were calculated as:

Relative strength=average signal of one probe/average signal of the subarray

Results are shown in FIG. 1. Relative strength is calculated on the Y axis. The relative strength of three NF-Kb probes (SEQ ID NO: 197, SEQ ID NO: 198, and SEQ ID NO: 99) increased in relation in nuclear extracts with added NF-κb. A mutant probe for NF-κB (SEQ ID NO: 202) did not increase and did decrease in relative strength with the addition of NF-κB.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A synthetic oligonucleotide comprising:
   a first sequence comprising a nucleic acid binding protein binding site;
   a second sequence comprising a binding site for a first PCR primer or an RNA polymerase promoter; and
   a third sequence comprising a tag sequence, wherein the tag sequence binds no nucleic acid binding protein and wherein the tag sequence is at least 15 nucleotides long;
   wherein at least the first sequence is double stranded and wherein the total length of the oligonucleotide is between 88 and 98 nucleotides.

2. The synthetic oligonucleotide of claim 1, wherein the second sequence is SEQ ID NO: 195 or SEQ ID NO: 196.

3. The synthetic oligonucleotide of claim 2, further comprising a fourth sequence, the fourth sequence comprising a binding site for a second PCR primer.

4. The synthetic oligonucleotide of claim 1, wherein the entire oligonucleotide is double-stranded.

5. The synthetic oligonucleotide of claim 1, comprising one or more copies of a single nucleic acid binding protein binding site.

6. The synthetic oligonucleotide of claim 1, wherein the oligonucleotide is between 90 and 98 nucleotides in length.

7. The synthetic oligonucleotide of claim 1, comprising SEQ ID NO: 1 and/or SEQ ID NO: 2.

8. The synthetic oligonucleotide of claim 1, wherein the tag sequence is 25 nucleotides in length.

9. The synthetic oligonucleotide of claim 8, comprising any of SEQ ID NOs: 3-98.

10. A method of detecting the presence of a nucleic acid binding protein in a sample, the method comprising:
    contacting a synthetic oligonucleotide of claim 1 with a sample, the sample comprising a nucleic acid binding protein;
    subjecting the sample to conditions that allow binding of the DNA binding protein to the synthetic oligonucleotide to form a nucleic acid binding protein/oligonucleotide complex;
    purifying the nucleic acid binding protein/oligonucleotide complex by electrophoresis;
    denaturing the nucleic acid binding protein/oligonucleotide complex;
    incorporating a label into the synthetic oligonucleotide;
    hybridizing the synthetic oligonucleotide to an array, wherein the array comprises a bound oligonucleotide, the bound oligonucleotide comprising the complement of the tag sequence and detecting the presence of the label;
    wherein the hybridizing the synthetic oligonucleotide to the array is performed after the purifying the nucleic acid binding protein/oligonucleotide complex by electrophoresis.

11. The method of claim 10, wherein the label is a fluorescent label.

12. The method of claim 10, wherein incorporating the label into the synthetic oligonucleotide comprises performing PCR amplification with primers complementary to a universal PCR forward primer sequence and a universal PCR reverse primer sequence.

13. The method of claim 10, wherein incorporating the label into the synthetic oligonucleotide comprises contacting the synthetic oligonucleotide with an RNA polymerase.

14. The method of claim 10, wherein the electrophoresis is performed using an electrophoresis device comprising:
   a cassette, wherein the cassette comprises a proximal end and a distal end opposite the proximal end, a front face and a back face and at least one chamber defined between the front face and the back face, the chamber having an upper portion and a lower portion, wherein the upper portion includes an upper opening at or near the proximal end of the cassette and the lower portion includes a lower opening at or near the distal end of the cassette, and wherein the front face comprises at least one window opening into the upper portion of the chamber;
   a first buffer solution in fluid contact with the lower opening of the lower portion;
   a second buffer solution in fluid contact with the window opening of the upper portion; and
   at least one electrode electrically coupled to each of the first and second buffer solutions.

15. A synthetic oligonucleotide library comprising:
   a first synthetic oligonucleotide of claim 1, the first synthetic oligonucleotide comprising a first nucleic acid binding protein binding site and a first tag sequence; and
   a second synthetic oligonucleotide of claim 1, the second synthetic oligonucleotide comprising a second nucleic acid binding protein binding site and a second tag sequence;
   wherein the first nucleic acid binding protein binding site and the second nucleic acid binding protein binding site are different sequences.

16. The synthetic oligonucleotide library of claim 15, wherein the first tag sequence is different from the second tag sequence.

17. The synthetic oligonucleotide library of claim 15, comprising two or more of the probes of SEQ ID NOs: 99-195 or SEQ ID NOs: 197-214.

18. A kit comprising:
   the synthetic oligonucleotide library of claim 15; and
   an array, the array comprising a third synthetic oligonucleotide comprising the complement of the first tag sequence and a fourth synthetic oligonucleotide comprising the complement of the second tag sequence; wherein the third synthetic oligonucleotide and the fourth synthetic oligonucleotide are each addressable on the microarray.

19. The kit of claim 18, wherein the third synthetic oligonucleotide and the fourth synthetic oligonucleotide comprise the complements of any of SEQ ID NOs: 3-98.

20. The synthetic oligonucleotide probe of claim 1, wherein a signal detected in a microarray is increased after the synthetic oligonucleotide probe is contacted with a nucleic acid binding protein that can bind the nucleic acid binding protein binding site.

* * * * *

SEQUENCE LISTING

```
<160> NUMBER OF SEQ ID NOS: 214

<210> SEQ ID NO 1
<211> LENGTH: 24
<212> TYPE: DNA
<213> ORGANISM: Artificial Sequence
<220> FEATURE:
<223> OTHER INFORMATION: Primer binding site

<400> SEQUENCE: 1
gtaatacgac tcactatagg gaga                                              24

<210> SEQ ID NO 2
<211> LENGTH: 24
<212> TYPE: DNA
<213> ORGANISM: Artificial Sequence
<220> FEATURE:
<223> OTHER INFORMATION: Primer Binding Site

<400> SEQUENCE: 2
cacttctata gtgtcaccta aatc                                              24

<210> SEQ ID NO 3
<211> LENGTH: 25
<212> TYPE: DNA
<213> ORGANISM: Artificial Sequence
<220> FEATURE:
<223> OTHER INFORMATION: Tag Sequence

<400> SEQUENCE: 3
tatcctttca ttcacagcca tgtgc                                             25

<210> SEQ ID NO 4
<211> LENGTH: 25
<212> TYPE: DNA
<213> ORGANISM: Artificial Sequence
<220> FEATURE:
<223> OTHER INFORMATION: Tag sequence

<400> SEQUENCE: 4
ccctctcctt ctccgataac gaaat                                             25

<210> SEQ ID NO 5
<211> LENGTH: 25
<212> TYPE: DNA
<213> ORGANISM: Artificial Sequence
<220> FEATURE:
<223> OTHER INFORMATION: Tag sequence

<400> SEQUENCE: 5
cccttcaatg gctcagatac acaca                                             25
```

<210> SEQ ID NO 6
<211> LENGTH: 25
<212> TYPE: DNA
<213> ORGANISM: Artificial Sequence
<220> FEATURE:
<223> OTHER INFORMATION: Tag sequence

<400> SEQUENCE: 6
ccgaggactg ctctcaactc aaact                                    25

<210> SEQ ID NO 7
<211> LENGTH: 25
<212> TYPE: DNA
<213> ORGANISM: Artificial Sequence
<220> FEATURE:
<223> OTHER INFORMATION: Tag sequence

<400> SEQUENCE: 7 ccctcttgc aggtattttg tcttg                                     25

<210> SEQ ID NO 8
<211> LENGTH: 25
<212> TYPE: DNA
<213> ORGANISM: Artificial Sequence
<220> FEATURE:
<223> OTHER INFORMATION: Tag sequence

<400> SEQUENCE: 8
ggctgccttg taataaacca tttcg                                    25

<210> SEQ ID NO 9
<211> LENGTH: 25
<212> TYPE: DNA
<213> ORGANISM: Artificial Sequence
<220> FEATURE:
<223> OTHER INFORMATION: Tag sequence

<400> SEQUENCE: 9
tcggcattta gatgcttcag ccaac                                    25

<210> SEQ ID NO 10
<211> LENGTH: 25
<212> TYPE: DNA
<213> ORGANISM: Artificial Sequence
<220> FEATURE:
<223> OTHER INFORMATION: Tag sequence

<400> SEQUENCE: 10
gtcatcagca tttcgtttag ccagc                                    25

<210> SEQ ID NO 11
<211> LENGTH: 25
<212> TYPE: DNA
<213> ORGANISM: Artificial Sequence
<220> FEATURE:
<223> OTHER INFORMATION: Tag sequence

<400> SEQUENCE: 11
ttcagggctt ctatctacga agtct                                    25

<210> SEQ ID NO 12
<211> LENGTH: 25
<212> TYPE: DNA
<213> ORGANISM: Artificial Sequence
<220> FEATURE:

```
<223> OTHER INFORMATION: Tag sequence

<400> SEQUENCE: 12
agttctcagt tgctttgaga agtct                                              25

<210> SEQ ID NO 13
<211> LENGTH: 25
<212> TYPE: DNA
<213> ORGANISM: Artificial Sequence
<220> FEATURE:
<223> OTHER INFORMATION: Tag sequence

<400> SEQUENCE: 13
tcgccatcat agatggtttg cctag                                              25

<210> SEQ ID NO 14
<211> LENGTH: 25
<212> TYPE: DNA
<213> ORGANISM: Artificial Sequence
<220> FEATURE:
<223> OTHER INFORMATION: Tag sequence

<400> SEQUENCE: 14
tcttcgcatc cactgctatg actag                                              25

<210> SEQ ID NO 15
<211> LENGTH: 25
<212> TYPE: DNA
<213> ORGANISM: Artificial Sequence
<220> FEATURE:
<223> OTHER INFORMATION: Tag sequence

<400> SEQUENCE: 15
tccagtggct ataggttgcg tatga                                              25

<210> SEQ ID NO 16
<211> LENGTH: 25
<212> TYPE: DNA
<213> ORGANISM: Artificial Sequence
<220> FEATURE:
<223> OTHER INFORMATION: Tag sequence

<400> SEQUENCE: 16
gagctcttcc ataggaggat tcgtt                                              25

<210> SEQ ID NO 17
<211> LENGTH: 25
<212> TYPE: DNA
<213> ORGANISM: Artificial Sequence
<220> FEATURE:
<223> OTHER INFORMATION: Tag sequence

<400> SEQUENCE: 17
atttatgctg cttcttcatc gcccc                                              25

<210> SEQ ID NO 18
<211> LENGTH: 25
<212> TYPE: DNA
<213> ORGANISM: Artificial Sequence
<220> FEATURE:
<223> OTHER INFORMATION: Tag sequence

<400> SEQUENCE: 18
agttgttgga gtatgatgtt cgccc                                              25
```

```
<210> SEQ ID NO 19
<211> LENGTH: 25
<212> TYPE: DNA
<213> ORGANISM: Artificial Sequence
<220> FEATURE:
<223> OTHER INFORMATION: Tag sequence

<400> SEQUENCE: 19
cgacttgttg acttgacatc tacgg                                              25

<210> SEQ ID NO 20
<211> LENGTH: 25
<212> TYPE: DNA
<213> ORGANISM: Artificial Sequence
<220> FEATURE:
<223> OTHER INFORMATION: Tag sequence

<400> SEQUENCE: 20
ttgcggttgt acacttacac tacgg                                              25

<210> SEQ ID NO 21
<211> LENGTH: 25
<212> TYPE: DNA
<213> ORGANISM: Artificial Sequence
<220> FEATURE:
<223> OTHER INFORMATION: Tag sequence

<400> SEQUENCE: 21
tcggttcgat accctcagat cctat                                              25

<210> SEQ ID NO 22
<211> LENGTH: 25
<212> TYPE: DNA
<213> ORGANISM: Artificial Sequence
<220> FEATURE:
<223> OTHER INFORMATION: Tag sequence

<400> SEQUENCE: 22
tttgtatcac attcgcaccc ctact                                              25

<210> SEQ ID NO 23
<211> LENGTH: 25
<212> TYPE: DNA
<213> ORGANISM: Artificial Sequence
<220> FEATURE:
<223> OTHER INFORMATION: Tag sequence

<400> SEQUENCE: 23
tccattcgtt gctacatttg cggca                                              25

<210> SEQ ID NO 24
<211> LENGTH: 25
<212> TYPE: DNA
<213> ORGANISM: Artificial Sequence
<220> FEATURE:
<223> OTHER INFORMATION: Tag sequence

<400> SEQUENCE: 24
ttgcttcttg acctatgtag cggca                                              25

<210> SEQ ID NO 25
<211> LENGTH: 25
<212> TYPE: DNA
<213> ORGANISM: Artificial Sequence
<220> FEATURE:
<223> OTHER INFORMATION: Tag sequence
```

```
<400> SEQUENCE: 25
gagactctga ttcgagctct tcact                                            25

<210> SEQ ID NO 26
<211> LENGTH: 25
<212> TYPE: DNA
<213> ORGANISM: Artificial Sequence
<220> FEATURE:
<223> OTHER INFORMATION: Tag sequence

<400> SEQUENCE: 26
catgtttcag aggtttacgg tcact                                            25

<210> SEQ ID NO 27
<211> LENGTH: 25
<212> TYPE: DNA
<213> ORGANISM: Artificial Sequence
<220> FEATURE:
<223> OTHER INFORMATION: Tag sequence

<400> SEQUENCE: 27
tgcttcgact ttgagacatt gacct                                            25

<210> SEQ ID NO 28
<211> LENGTH: 25
<212> TYPE: DNA
<213> ORGANISM: Artificial Sequence
<220> FEATURE:
<223> OTHER INFORMATION: Tag sequence

<400> SEQUENCE: 28
cggtttacga ttcataccct gacct                                            25

<210> SEQ ID NO 29
<211> LENGTH: 25
<212> TYPE: DNA
<213> ORGANISM: Artificial Sequence
<220> FEATURE:
<223> OTHER INFORMATION: Tag sequence

<400> SEQUENCE: 29
tctgatccat ggttgtagga gaacg                                            25

<210> SEQ ID NO 30
<211> LENGTH: 25
<212> TYPE: DNA
<213> ORGANISM: Artificial Sequence
<220> FEATURE:
<223> OTHER INFORMATION: Tag sequence

<400> SEQUENCE: 30
tcgttggttg agttaccgat cgaat                                            25

<210> SEQ ID NO 31
<211> LENGTH: 25
<212> TYPE: DNA
<213> ORGANISM: Artificial Sequence
<220> FEATURE:
<223> OTHER INFORMATION: Tag sequence

<400> SEQUENCE: 31
cctgttccag tagatgtagg cactt                                            25

<210> SEQ ID NO 32
<211> LENGTH: 25
```

```
<212> TYPE: DNA
<213> ORGANISM: Artificial Sequence
<220> FEATURE:
<223> OTHER INFORMATION: Tag sequence

<400> SEQUENCE: 32
ggagctctgg atttagctac cactt                                         25

<210> SEQ ID NO 33
<211> LENGTH: 25
<212> TYPE: DNA
<213> ORGANISM: Artificial Sequence
<220> FEATURE:
<223> OTHER INFORMATION: Tag sequence

<400> SEQUENCE: 33
agagccttcg atgtgcttta ggatc                                         25

<210> SEQ ID NO 34
<211> LENGTH: 25
<212> TYPE: DNA
<213> ORGANISM: Artificial Sequence
<220> FEATURE:
<223> OTHER INFORMATION: Tag sequence

<400> SEQUENCE: 34
tggcatcttc ctttagtctg cgatc                                         25

<210> SEQ ID NO 35
<211> LENGTH: 25
<212> TYPE: DNA
<213> ORGANISM: Artificial Sequence
<220> FEATURE:
<223> OTHER INFORMATION: Tag sequence

<400> SEQUENCE: 35
cgatccgata gggtttgatt gctca                                         25

<210> SEQ ID NO 36
<211> LENGTH: 25
<212> TYPE: DNA
<213> ORGANISM: Artificial Sequence
<220> FEATURE:
<223> OTHER INFORMATION: Tag sequence

<400> SEQUENCE: 36
atcttctcac ttactatggc gctca                                         25

<210> SEQ ID NO 37
<211> LENGTH: 25
<212> TYPE: DNA
<213> ORGANISM: Artificial Sequence
<220> FEATURE:
<223> OTHER INFORMATION: Tag sequence

<400> SEQUENCE: 37
tatggcagag tgttcggatc atgtg                                         25

<210> SEQ ID NO 38
<211> LENGTH: 25
<212> TYPE: DNA
<213> ORGANISM: Artificial Sequence
<220> FEATURE:
<223> OTHER INFORMATION: Tag sequence

<400> SEQUENCE: 38
```
ttgccgagat gagatttctg agtgg    25

<210> SEQ ID NO 39
<211> LENGTH: 25
<212> TYPE: DNA
<213> ORGANISM: Artificial Sequence
<220> FEATURE:
<223> OTHER INFORMATION: Tag sequence

<400> SEQUENCE: 39
gcttctcttc ttcgggatct tgagt    25

<210> SEQ ID NO 40
<211> LENGTH: 25
<212> TYPE: DNA
<213> ORGANISM: Artificial Sequence
<220> FEATURE:
<223> OTHER INFORMATION: Tag sequence

<400> SEQUENCE: 40
tgttcaccga tgacatttct cgagt    25

<210> SEQ ID NO 41
<211> LENGTH: 25
<212> TYPE: DNA
<213> ORGANISM: Artificial Sequence
<220> FEATURE:
<223> OTHER INFORMATION: Tag sequence

<400> SEQUENCE: 41
gcagaggtat tcactacgtc tctgt    25

<210> SEQ ID NO 42
<211> LENGTH: 25
<212> TYPE: DNA
<213> ORGANISM: Artificial Sequence
<220> FEATURE:
<223> OTHER INFORMATION: Tag sequence

<400> SEQUENCE: 42
cagctcatat tcggaggatg ttggt    25

<210> SEQ ID NO 43
<211> LENGTH: 25
<212> TYPE: DNA
<213> ORGANISM: Artificial Sequence
<220> FEATURE:
<223> OTHER INFORMATION: Tag sequence

<400> SEQUENCE: 43 atcctcccctt gtgttcatag gacag    25

<210> SEQ ID NO 44
<211> LENGTH: 25
<212> TYPE: DNA
<213> ORGANISM: Artificial Sequence
<220> FEATURE:
<223> OTHER INFORMATION: Tag sequence

<400> SEQUENCE: 44
acatgatcca tgtgtagtgc tcctc    25

<210> SEQ ID NO 45
<211> LENGTH: 25
<212> TYPE: DNA
<213> ORGANISM: Artificial Sequence

```
<220> FEATURE:
<223> OTHER INFORMATION: Tag sequence

<400> SEQUENCE: 45
cacctatggg gtatcccgag tattt                                              25

<210> SEQ ID NO 46
<211> LENGTH: 25
<212> TYPE: DNA
<213> ORGANISM: Artificial Sequence
<220> FEATURE:
<223> OTHER INFORMATION: Tag sequence

<400> SEQUENCE: 46
ggtacggacc tatatccctg gattt                                              25

<210> SEQ ID NO 47
<211> LENGTH: 25
<212> TYPE: DNA
<213> ORGANISM: Artificial Sequence
<220> FEATURE:
<223> OTHER INFORMATION: Tag sequence

<400> SEQUENCE: 47
tgtgaggagt tgatgacgag gtgtt                                              25

<210> SEQ ID NO 48
<211> LENGTH: 25
<212> TYPE: DNA
<213> ORGANISM: Artificial Sequence
<220> FEATURE:
<223> OTHER INFORMATION: Tag sequence

<400> SEQUENCE: 48
ccgtactttc cgactgtact gtcaa                                              25

<210> SEQ ID NO 49
<211> LENGTH: 25
<212> TYPE: DNA
<213> ORGANISM: Artificial Sequence
<220> FEATURE:
<223> OTHER INFORMATION: Tag sequence

<400> SEQUENCE: 49
acttcgcgga cctattatac gagtt                                              25

<210> SEQ ID NO 50
<211> LENGTH: 25
<212> TYPE: DNA
<213> ORGANISM: Artificial Sequence
<220> FEATURE:
<223> OTHER INFORMATION: Tag sequence

<400> SEQUENCE: 50
agatcgtcga ttgcagatac ttcgt                                              25

<210> SEQ ID NO 51
<211> LENGTH: 25
<212> TYPE: DNA
<213> ORGANISM: Artificial Sequence
<220> FEATURE:
<223> OTHER INFORMATION: Tag sequence

<400> SEQUENCE: 51
agctgatcag gtattgggtt taggt                                              25
```

<210> SEQ ID NO 52
<211> LENGTH: 25
<212> TYPE: DNA
<213> ORGANISM: Artificial Sequence
<220> FEATURE:
<223> OTHER INFORMATION: Tag sequence

<400> SEQUENCE: 52
gaccagtggc atctaggtta gttct                                    25

<210> SEQ ID NO 53
<211> LENGTH: 25
<212> TYPE: DNA
<213> ORGANISM: Artificial Sequence
<220> FEATURE:
<223> OTHER INFORMATION: Tag sequence

<400> SEQUENCE: 53
tcgagtgaca atgggtttcc ttcag                                    25

<210> SEQ ID NO 54
<211> LENGTH: 25
<212> TYPE: DNA
<213> ORGANISM: Artificial Sequence
<220> FEATURE:
<223> OTHER INFORMATION: Tag sequence

<400> SEQUENCE: 54
ttagggttcc ctactccatt gagag                                    25

<210> SEQ ID NO 55
<211> LENGTH: 25
<212> TYPE: DNA
<213> ORGANISM: Artificial Sequence
<220> FEATURE:
<223> OTHER INFORMATION: Tag sequence

<400> SEQUENCE: 55
ggagccatgg attctcacat ctttt                                    25

<210> SEQ ID NO 56
<211> LENGTH: 25
<212> TYPE: DNA
<213> ORGANISM: Artificial Sequence
<220> FEATURE:
<223> OTHER INFORMATION: Tag sequence

<400> SEQUENCE: 56
tacttgtttg tgcatcccca ttttt                                    25

<210> SEQ ID NO 57
<211> LENGTH: 25
<212> TYPE: DNA
<213> ORGANISM: Artificial Sequence
<220> FEATURE:
<223> OTHER INFORMATION: Tag sequence

<400> SEQUENCE: 57
attcaggagt catagtcagc tctgt                                    25

<210> SEQ ID NO 58
<211> LENGTH: 25
<212> TYPE: DNA
<213> ORGANISM: Artificial Sequence
<220> FEATURE:
<223> OTHER INFORMATION: Tag sequence

<400> SEQUENCE: 58
catttgacac gactcttttc cagct                                              25

<210> SEQ ID NO 59
<211> LENGTH: 25
<212> TYPE: DNA
<213> ORGANISM: Artificial Sequence
<220> FEATURE:
<223> OTHER INFORMATION: Tag sequence

<400> SEQUENCE: 59
tcccactatc catgatcagt ttggt                                              25

<210> SEQ ID NO 60
<211> LENGTH: 25
<212> TYPE: DNA
<213> ORGANISM: Artificial Sequence
<220> FEATURE:
<223> OTHER INFORMATION: Tag sequence

<400> SEQUENCE: 60
ctcccatgga tgtcgtatac ctagt                                              25

<210> SEQ ID NO 61
<211> LENGTH: 25
<212> TYPE: DNA
<213> ORGANISM: Artificial Sequence
<220> FEATURE:
<223> OTHER INFORMATION: Tag sequence

<400> SEQUENCE: 61
atttcgacgc tttatgacga tcctg                                              25

<210> SEQ ID NO 62
<211> LENGTH: 25
<212> TYPE: DNA
<213> ORGANISM: Artificial Sequence
<220> FEATURE:
<223> OTHER INFORMATION: Tag sequence

<400> SEQUENCE: 62
gcccgatatt gccgatctac ttact                                              25

<210> SEQ ID NO 63
<211> LENGTH: 25
<212> TYPE: DNA
<213> ORGANISM: Artificial Sequence
<220> FEATURE:
<223> OTHER INFORMATION: Tag sequence

<400> SEQUENCE: 63
gtgtcgatga tattcggctg agtga                                              25

<210> SEQ ID NO 64
<211> LENGTH: 25
<212> TYPE: DNA
<213> ORGANISM: Artificial Sequence
<220> FEATURE:
<223> OTHER INFORMATION: Tag sequence

<400> SEQUENCE: 64
ctgttgcacg tatttcggag agtga                                              25

<210> SEQ ID NO 65

<211> LENGTH: 25
<212> TYPE: DNA
<213> ORGANISM: Artificial Sequence
<220> FEATURE:
<223> OTHER INFORMATION: Tag sequence

<400> SEQUENCE: 65
gcctggtatt ttctgattgc acctg                                          25

<210> SEQ ID NO 66
<211> LENGTH: 25
<212> TYPE: DNA
<213> ORGANISM: Artificial Sequence
<220> FEATURE:
<223> OTHER INFORMATION: Tag sequence

<400> SEQUENCE: 66
ttctgtgcta ggggacgata tacat                                          25

<210> SEQ ID NO 67
<211> LENGTH: 25
<212> TYPE: DNA
<213> ORGANISM: Artificial Sequence
<220> FEATURE:
<223> OTHER INFORMATION: Tag sequence

<400> SEQUENCE: 67
tgatatcggt agagcacgtt tgtgc                                          25

<210> SEQ ID NO 68
<211> LENGTH: 25
<212> TYPE: DNA
<213> ORGANISM: Artificial Sequence
<220> FEATURE:
<223> OTHER INFORMATION: Tag sequence

<400> SEQUENCE: 68
tcccctacac atttcgtgat tgtca                                          25

<210> SEQ ID NO 69
<211> LENGTH: 25
<212> TYPE: DNA
<213> ORGANISM: Artificial Sequence
<220> FEATURE:
<223> OTHER INFORMATION: Tag sequence

<400> SEQUENCE: 69
ggtgtaggtt tcacagtctc caaga                                          25

<210> SEQ ID NO 70
<211> LENGTH: 25
<212> TYPE: DNA
<213> ORGANISM: Artificial Sequence
<220> FEATURE:
<223> OTHER INFORMATION: Tag sequence

<400> SEQUENCE: 70
ccgcttgtga cttgatgatc acaga                                          25

<210> SEQ ID NO 71
<211> LENGTH: 25
<212> TYPE: DNA
<213> ORGANISM: Artificial Sequence
<220> FEATURE:
<223> OTHER INFORMATION: Tag sequence

<400> SEQUENCE: 71

-continued gcgatcctga ttacccgatg tatgt          25

<210> SEQ ID NO 72
<211> LENGTH: 25
<212> TYPE: DNA
<213> ORGANISM: Artificial Sequence
<220> FEATURE:
<223> OTHER INFORMATION: Tag sequence

<400> SEQUENCE: 72
attgttgttt cctgcgtgtt aggac          25

<210> SEQ ID NO 73
<211> LENGTH: 25
<212> TYPE: DNA
<213> ORGANISM: Artificial Sequence
<220> FEATURE:
<223> OTHER INFORMATION: Tag sequence

<400> SEQUENCE: 73
accgcgttag attcgtagta tgctg          25

<210> SEQ ID NO 74
<211> LENGTH: 25
<212> TYPE: DNA
<213> ORGANISM: Artificial Sequence
<220> FEATURE:
<223> OTHER INFORMATION: Tag sequence

<400> SEQUENCE: 74
atcgttggcc ttatgagtct cagag          25

<210> SEQ ID NO 75
<211> LENGTH: 25
<212> TYPE: DNA
<213> ORGANISM: Artificial Sequence
<220> FEATURE:
<223> OTHER INFORMATION: Tag sequence

<400> SEQUENCE: 75
tttcagcttt cggaagatca cgtcg          25

<210> SEQ ID NO 76
<211> LENGTH: 25
<212> TYPE: DNA
<213> ORGANISM: Artificial Sequence
<220> FEATURE:
<223> OTHER INFORMATION: Tag sequence

<400> SEQUENCE: 76
ttcgtgcatg agatttcatc cagtg          25

<210> SEQ ID NO 77
<211> LENGTH: 25
<212> TYPE: DNA
<213> ORGANISM: Artificial Sequence
<220> FEATURE:
<223> OTHER INFORMATION: Tag sequence

<400> SEQUENCE: 77
ggcatcctgt tagactgaga tggtt          25

<210> SEQ ID NO 78
<211> LENGTH: 25
<212> TYPE: DNA

```
<213> ORGANISM: Artificial Sequence
<220> FEATURE:
<223> OTHER INFORMATION: Tag sequnce

<400> SEQUENCE: 78
acctcggtta gtacttcacc tcaac                                    25

<210> SEQ ID NO 79
<211> LENGTH: 25
<212> TYPE: DNA
<213> ORGANISM: Artificial Sequence
<220> FEATURE:
<223> OTHER INFORMATION: Tag sequence

<400> SEQUENCE: 79
ttgcagatgt cgactactta cctgc                                    25

<210> SEQ ID NO 80
<211> LENGTH: 25
<212> TYPE: DNA
<213> ORGANISM: Artificial Sequence
<220> FEATURE:
<223> OTHER INFORMATION: Tag sequence

<400> SEQUENCE: 80
tgggcatacc tagacttctg cgtta                                    25

<210> SEQ ID NO 81
<211> LENGTH: 25
<212> TYPE: DNA
<213> ORGANISM: Artificial Sequence
<220> FEATURE:
<223> OTHER INFORMATION: Tag sequence

<400> SEQUENCE: 81
catgcttcat tgtctagatg ccagc                                    25

<210> SEQ ID NO 82
<211> LENGTH: 25
<212> TYPE: DNA
<213> ORGANISM: Artificial Sequence
<220> FEATURE:
<223> OTHER INFORMATION: Tag sequence

<400> SEQUENCE: 82
cagctacagt ctttagtttg ccagc                                    25

<210> SEQ ID NO 83
<211> LENGTH: 25
<212> TYPE: DNA
<213> ORGANISM: Artificial Sequence
<220> FEATURE:
<223> OTHER INFORMATION: Tag sequence

<400> SEQUENCE: 83
catgttgcat cactctttgc aggag                                    25

<210> SEQ ID NO 84
<211> LENGTH: 25
<212> TYPE: DNA
<213> ORGANISM: Artificial Sequence
<220> FEATURE:
<223> OTHER INFORMATION: Tag sequence

<400> SEQUENCE: 84
atgatctacc cgatcgtatg tgctc                                    25
```

<210> SEQ ID NO 85
<211> LENGTH: 25
<212> TYPE: DNA
<213> ORGANISM: Artificial Sequence
<220> FEATURE:
<223> OTHER INFORMATION: Tag sequence

<400> SEQUENCE: 85
tggtatcgca gttgatatga tggcg                                  25

<210> SEQ ID NO 86
<211> LENGTH: 25
<212> TYPE: DNA
<213> ORGANISM: Artificial Sequence
<220> FEATURE:
<223> OTHER INFORMATION: Tag seqence

<400> SEQUENCE: 86
agagttggta tagagtgttt gggcg                                  25

<210> SEQ ID NO 87
<211> LENGTH: 25
<212> TYPE: DNA
<213> ORGANISM: Artificial Sequence
<220> FEATURE:
<223> OTHER INFORMATION: Tag sequence

<400> SEQUENCE: 87
tcgattcgat tgtctttagc cagcc                                  25

<210> SEQ ID NO 88
<211> LENGTH: 25
<212> TYPE: DNA
<213> ORGANISM: Artificial Sequence
<220> FEATURE:
<223> OTHER INFORMATION: Tag sequence

<400> SEQUENCE: 88
acttgcttga ctcttggtat ggacg                                  25

<210> SEQ ID NO 89
<211> LENGTH: 25
<212> TYPE: DNA
<213> ORGANISM: Artificial Sequence
<220> FEATURE:
<223> OTHER INFORMATION: Tag sequence

<400> SEQUENCE: 89
attgctcctt cactccgcat agaac                                  25

<210> SEQ ID NO 90
<211> LENGTH: 25
<212> TYPE: DNA
<213> ORGANISM: Artificial Sequence
<220> FEATURE:
<223> OTHER INFORMATION: Tag sequence

<400> SEQUENCE: 90
ctctccgctt atatcacact ccagt                                  25

<210> SEQ ID NO 91
<211> LENGTH: 25
<212> TYPE: DNA
<213> ORGANISM: Artificial Sequence
<220> FEATURE:

```
<223> OTHER INFORMATION: Tag sequence

<400> SEQUENCE: 91
tgttgaagag ctgggtatct tcgga                                      25

<210> SEQ ID NO 92
<211> LENGTH: 25
<212> TYPE: DNA
<213> ORGANISM: Artificial Sequence
<220> FEATURE:
<223> OTHER INFORMATION: Tag sequence

<400> SEQUENCE: 92
atgcactgat tagtcctact gtggt                                      25

<210> SEQ ID NO 93
<211> LENGTH: 25
<212> TYPE: DNA
<213> ORGANISM: Artificial Sequence
<220> FEATURE:
<223> OTHER INFORMATION: Tag sequence

<400> SEQUENCE: 93
cgcagattcg acattgcttg ttcag                                      25

<210> SEQ ID NO 94
<211> LENGTH: 25
<212> TYPE: DNA
<213> ORGANISM: Artificial Sequence
<220> FEATURE:
<223> OTHER INFORMATION: Tag sequence

<400> SEQUENCE: 94
ctgtggtagg attacttggt ccaag                                      25

<210> SEQ ID NO 95
<211> LENGTH: 25
<212> TYPE: DNA
<213> ORGANISM: Artificial Sequence
<220> FEATURE:
<223> OTHER INFORMATION: Tag sequence

<400> SEQUENCE: 95
tagtgactta gcgttaggtt gggag                                      25

<210> SEQ ID NO 96
<211> LENGTH: 25
<212> TYPE: DNA
<213> ORGANISM: Artificial Sequence
<220> FEATURE:
<223> OTHER INFORMATION: Tag sequence

<400> SEQUENCE: 96
tcttgtctac cactgagcgt gtaca                                      25

<210> SEQ ID NO 97
<211> LENGTH: 25
<212> TYPE: DNA
<213> ORGANISM: Artificial Sequence
<220> FEATURE:
<223> OTHER INFORMATION: Tag sequence

<400> SEQUENCE: 97
cgagtttgtc ccttctgtgt agcat                                      25
```

```
<210> SEQ ID NO 98
<211> LENGTH: 25
<212> TYPE: DNA
<213> ORGANISM: Artificial Sequence
<220> FEATURE:
<223> OTHER INFORMATION: Tag sequence

<400> SEQUENCE: 98
ttagagcctt ttgcaggact gatcc                                            25

<210> SEQ ID NO 99
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 99
gtaatacgac tcactatagg gagacctctc ggaaagtccc ctctcaagac aaaatacctg      60 caagagggc acttctatag tgtcacctaa atc                                    93

<210> SEQ ID NO 100
<211> LENGTH: 93
<212> TYPE: DNA
<213> ORGANISM: Artificial Sequence
<220> FEATURE:
<223> OTHER INFORMATION: Oligonucleotide Probe

<400> SEQUENCE: 100
gtaatacgac tcactatagg gagacctctc ggaaagtccc ctctatttcg ttatcggaga      60
aggagagggc acttctatag tgtcacctaa atc                                   93

<210> SEQ ID NO 101
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 101
gtaatacgac tcactatagg gagatacaga acatgtccca acatgttggc tgaagcatct     60
aaatgccgac acttctatag tgtcacctaa atc                                   93

<210> SEQ ID NO 102
<211> LENGTH: 93
<212> TYPE: DNA
<213> ORGANISM: Artificial Sequence
<220> FEATURE:
<223> OTHER INFORMATION: Oligonucleotide Probe

<400> SEQUENCE: 102
gtaatacgac tcactatagg gagatacaga acatgtctaa gcatgctggc taaacgaaat     60
gctgatgacc acttctatag tgtcacctaa atc                                   93

<210> SEQ ID NO 103
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 103
gtaatacgac tcactatagg gagacaaaaa gaacaccctg taccagactt cgtagataga     60
```

```
agccctgaac acttctatag tgtcacctaa atc                           93
```

<210> SEQ ID NO 104
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 104

```
gtaatacgac tcactatagg gagacaaaaa gaacaccctg taccagactt ctcaaagcaa   60
ctgagaactc acttctatag tgtcacctaa atc                               93
```

<210> SEQ ID NO 105
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 105

```
gtaatacgac tcactatagg gagagattgc ctgacgtcag agagctaggc aaaccatcta   60
tgatggcgac acttctatag tgtcacctaa atc                               93
```

<210> SEQ ID NO 106
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 106

```
gtaatacgac tcactatagg gagagattgc ctgacgtcag agagctagtc atagcagtgg   60
atgcgaagac acttctatag tgtcacctaa atc                               93
```

<210> SEQ ID NO 107
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 107

```
gtaatacgac tcactatagg gagactagtg atgagtcagc cggatcatac gcaacctata   60
gccactggac acttctatag tgtcacctaa atc                               93
```

<210> SEQ ID NO 108
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 108

```
gtaatacgac tcactatagg gagaggcttg atgactcagc cggaaacgaa tcctcctatg   60
gaagagctcc acttctatag tgtcacctaa atc                               93
```

<210> SEQ ID NO 109

<400> SEQUENCE: 109

000

```
<210> SEQ ID NO 110
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 110
gtaatacgac tcactatagg gagagatcca gcggggcga gcggggcga acatcatact      60 ccaacaactc acttctatag tgtcacctaa atc                                93

<210> SEQ ID NO 111
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 111
gtaatacgac tcactatagg gagatcgtac tgaccgcccg cggcccgtag atgtcaagtc    60
aacaagtcgc acttctatag tgtcacctaa atc                                93

<210> SEQ ID NO 112
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 112
gtaatacgac tcactatagg gagatcgtac tgaccgcccg cggcccgtag tgtaagtgta    60
caaccgcaac acttctatag tgtcacctaa atc                                93

<210> SEQ ID NO 113
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 113
gtaatacgac tcactatagg gagagatcca tatattaagt atatatagga tctgagggta    60
tcgaaccgac acttctatag tgtcacctaa atc                                93

<210> SEQ ID NO 114
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 114
gtaatacgac tcactatagg gagagtatat aagtagttgt aagtagtagg ggtgcgaatg    60
tgatacaaac acttctatag tgtcacctaa atc                                93

<210> SEQ ID NO 115
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 115
```

```
gtaatacgac tcactatagg gagagagata tcatcttgca aggatgccgc aaatgtagca    60
acgaatggac acttctatag tgtcacctaa atc                                 93
```

<210> SEQ ID NO 116
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 116

```
gtaatacgac tcactatagg gagagagata tcatcttgca aggatgccgc tacataggtc    60
aagaagcaac acttctatag tgtcacctaa atc                                 93
```

<210> SEQ ID NO 117
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 117

```
gtaatacgac tcactatagg gagatacagg cataacggtt ccgtagtgaa gagctcgaat    60
cagagtctcc acttctatag tgtcacctaa atc                                 93
```

<210> SEQ ID NO 118
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 118

```
gtaatacgac tcactatagg gagatacagg cataacggtt ccgtagtgac cgtaaacctc    60
tgaaacatgc acttctatag tgtcacctaa atc                                 93
```

<210> SEQ ID NO 119
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 119

```
gtaatacgac tcactatagg gagaaatgca caaaactagg tcaaaggtca atgtctcaaa    60
gtcgaagcac acttctatag tgtcacctaa atc                                 93
```

<210> SEQ ID NO 120
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 120

```
gtaatacgac tcactatagg gagaaatgca caaaactagg tcaaaggtca gggtatgaat    60
cgtaaaccgc acttctatag tgtcacctaa atc                                 93
```

<210> SEQ ID NO 121
<211> LENGTH: 93
<212> TYPE: DNA

<213> ORGANISM: Artificial Sequence
<220> FEATURE:
<223> OTHER INFORMATION: Oligonucleotide probe

<400> SEQUENCE: 121
gtaatacgac tcactatagg gagagcggac caggacaaag gtcacgttct cctacaacca    60
tggatcagac acttctatag tgtcacctaa atc    93

<210> SEQ ID NO 122
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 122
gtaatacgac tcactatagg gagaagtgag ccgctcacag gtcaattcga tcggtaactc    60
aaccaacgac acttctatag tgtcacctaa atc    93

<210> SEQ ID NO 123
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 123
gtaatacgac tcactatagg gagatgtcga atgcaaatca ctagacagag acgtagtgaa    60
tacctctgcc acttctatag tgtcacctaa atc    93

<210> SEQ ID NO 124
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 124
gtaatacgac tcactatagg gagatgtcga atgcaaatca ctagaccaac atcctccgaa    60
tatgagctgc acttctatag tgtcacctaa atc    93

<210> SEQ ID NO 125
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 125
gtaatacgac tcactatagg gagatctgta cgtgtccaca ctcactgtcc tatgaacaca    60
agggaggatc acttctatag tgtcacctaa atc    93

<210> SEQ ID NO 126
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 126
gtaatacgac tcactatagg gagatctgta cgtgaccaca ctcagaggag cactacacat    60
ggatcatgtc acttctatag tgtcacctaa atc    93

<210> SEQ ID NO 127
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 127
gtaatacgac tcactatagg gagatgagaa agggcgcgaa acttaaatac tcgggatacc    60
ccataggtgc acttctatag tgtcacctaa atc                                 93

<210> SEQ ID NO 128
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 128
gtaatacgac tcactatagg gagatgagaa agggcgcgaa acttaaatcc agggatatag    60
gtccgtaccc acttctatag tgtcacctaa atc                                 93

<210> SEQ ID NO 129
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 129
gtaatacgac tcactatagg gagatgcaga ttgcgcaatc tgcaaacacc tcgtcatcaa    60
ctcctcacac acttctatag tgtcacctaa atc                                 93

<210> SEQ ID NO 130
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 130
gtaatacgac tcactatagg gagagcgcaa tgaattgagc aatgttgaca gtacagtcgg    60
aaagtacggc acttctatag tgtcacctaa atc                                 93

<210> SEQ ID NO 131
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 131
gtaatacgac tcactatagg gagagaaaat tcctagagag cataacctaa acccaatacc    60
tgatcagctc acttctatag tgtcacctaa atc                                 93

<210> SEQ ID NO 132
<211> LENGTH: 93
<212> TYPE: DNA
<213> ORGANISM: Artificial Sequence
<220> FEATURE:
<223> OTHER INFORMATION: Oligonucleotide probe

```
<400> SEQUENCE: 132
gtaatacgac tcactatagg gagagaaaat tcctagagag cataagaact aacctagatg    60
ccactggtcc acttctatag tgtcacctaa atc                                 93

<210> SEQ ID NO 133
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 133
gtaatacgac tcactatagg gagaggatgt ccatattagg acatctgaag gaaacccatt    60
gtcactcgac acttctatag tgtcacctaa atc                                 93

<210> SEQ ID NO 134
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 134
gtaatacgac tcactatagg gagaggatgt ccatattagg acatctctca atggagtagg    60
gaaccctaac acttctatag tgtcacctaa atc                                 93

<210> SEQ ID NO 135
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 135
gtaatacgac tcactatagg gagactggat ataaataaat attgaaaaga tgtgagaatc    60
catggctccc acttctatag tgtcacctaa atc                                 93

<210> SEQ ID NO 136
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 136
gtaatacgac tcactatagg gagactgctt tctgtaaaca tgtgaaaaat ggggatgcac    60
aaacaagtac acttctatag tgtcacctaa atc                                 93

<210> SEQ ID NO 137
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 137
gtaatacgac tcactatagg gagacgtaat atctgtgagg ctaaacagag ctgactatga    60
ctcctgaatc acttctatag tgtcacctaa atc                                 93

<210> SEQ ID NO 138
<211> LENGTH: 93
```

```
<212> TYPE: DNA
<213> ORGANISM: Artificial Sequence
<220> FEATURE:
<223> OTHER INFORMATION: Oligonucleotide probe

<400> SEQUENCE: 138
gtaatacgac tcactatagg gagaatatct gtgaggctaa acagagctgg aaaagagtcg    60
tgtcaaatgc acttctatag tgtcacctaa atc                                 93

<210> SEQ ID NO 139
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 139
gtaatacgac tcactatagg gagaaagtaa acaaacaaa caaaaccaaa ctgatcatgg     60
atagtgggac acttctatag tgtcacctaa atc                                 93

<210> SEQ ID NO 140
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 140
gtaatacgac tcactatagg gagacaaggt aaacaaacca tcctactagg tatacgacat    60
ccatgggagc acttctatag tgtcacctaa atc                                 93

<210> SEQ ID NO 141
<211> LENGTH: 93
<212> TYPE: DNA
<213> ORGANISM: Artificial Sequence
<220> FEATURE:
<223> OTHER INFORMATION: Oligonucelotide probe

<400> SEQUENCE: 141
gtaatacgac tcactatagg gagatgtagc tagaacatcc tgtacaggat cgtcataaag    60
cgtcgaaatc acttctatag tgtcacctaa atc                                 93

<210> SEQ ID NO 142
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 142
gtaatacgac tcactatagg gagagctaga acatcctgta caggagtaag tagatcggca    60
atatcgggcc acttctatag tgtcacctaa atc                                 93

<210> SEQ ID NO 143
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 143
gtaatacgac tcactatagg gagagggtag ggttcaccga aagttcactc agccgaatat    60
```

```
catcgacacc acttctatag tgtcacctaa atc                              93
```

<210> SEQ ID NO 144
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 144

```
gtaatacgac tcactatagg gagagggtag ggttcaccga aagttcactc tccgaaatac   60
gtgcaacagc acttctatag tgtcacctaa atc                              93
```

<210> SEQ ID NO 145
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 145

```
gtaatacgac tcactatagg gagatgtgaa caggtgcttg tgaacaggtg caatcagaaa   60
ataccaggcc acttctatag tgtcacctaa atc                              93
```

<210> SEQ ID NO 146
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 146

```
gtaatacgac tcactatagg gagagtaact cgctccacct gtaaatgtat atcgtccct   60 agcacagaac acttctatag tgtcacctaa atc                              93
```

<210> SEQ ID NO 147
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 147

```
gtaatacgac tcactatagg gagacatgtt atacatattc ctgtaagtgc ctacatctac   60
tggaacaggc acttctatag tgtcacctaa atc                              93
```

<210> SEQ ID NO 148
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 148

```
gtaatacgac tcactatagg gagatccgta ttcccgtcaa tgcaaagtgg tagctaaatc   60
cagagctccc acttctatag tgtcacctaa atc                              93
```

<210> SEQ ID NO 149
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 149
gtaatacgac tcactatagg gagagatcct tctgggaatt cctagatcct aaagcacatc    60
gaaggctctc acttctatag tgtcacctaa atc    93

<210> SEQ ID NO 150
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 150
gtaatacgac tcactatagg gagagatcct tctgggaatt cctagatcgc agactaaagg    60
aagatgccac acttctatag tgtcacctaa atc    93

<210> SEQ ID NO 151
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 151
gtaatacgac tcactatagg gagagcctga tttccccgaa atgatgagca atcaaaccct    60
atcggatcgc acttctatag tgtcacctaa atc    93

<210> SEQ ID NO 152
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 152
gtaatacgac tcactatagg gagagcctga tttccccgaa atgatgagcg ccatagtaag    60
tgagaagatc acttctatag tgtcacctaa atc    93

<210> SEQ ID NO 153
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 153
gtaatacgac tcactatagg gagaagattt ctaggaattc aatccacatg atccgaacac    60
tctgccatac acttctatag tgtcacctaa atc    93

<210> SEQ ID NO 154
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 154
gtaatacgac tcactatagg gagaagattt ctaggaattc aatcccactc agaaatctca    60
tctcggcaac acttctatag tgtcacctaa atc    93

<210> SEQ ID NO 155

```
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 155
gtaatacgac tcactatagg gagagtattt cccagaaaag gaacactcaa gatcccgaag      60
aagagaagcc acttctatag tgtcacctaa atc                                  93

<210> SEQ ID NO 156
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 156
gtaatacgac tcactatagg gagagtattt cccagaaaag gaacactcga gaaatgtcat      60
cggtgaacac acttctatag tgtcacctaa atc                                  93

<210> SEQ ID NO 157
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 157
gtaatacgac tcactatagg gagaaagaat atcattagca tgcagcacaa acgtgctcta      60
ccgatatcac acttctatag tgtcacctaa atc                                  93

<210> SEQ ID NO 158
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 158
gtaatacgac tcactatagg gagacacagc tcattaacgc gcaatgacaa tcacgaaatg      60
tgtaggggac acttctatag tgtcacctaa atc                                  93

<210> SEQ ID NO 159
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 159
gtaatacgac tcactatagg gagaccgtac gtgattggtt aatctcttgg agactgtgaa      60
acctacaccc acttctatag tgtcacctaa atc                                  93

<210> SEQ ID NO 160
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 160
gtaatacgac tcactatagg gagaccatga atggccatga atggtctgtg atcatcaagt      60
```
cacaagcggc acttctatag tgtcacctaa atc                                    93

<210> SEQ ID NO 161
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 161
gtaatacgac tcactatagg gagataataa atgaaatcga tgtcacatac atcgggtaat      60
caggatcgcc acttctatag tgtcacctaa atc                                    93

<210> SEQ ID NO 162
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 162
gtaatacgac tcactatagg gagaaattgg ctaataatca ttgggtccta acacgcagga      60
aacaacaatc acttctatag tgtcacctaa atc                                    93

<210> SEQ ID NO 163
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 163
gtaatacgac tcactatagg gagacggatg ctaccgcgcg gtggcagcat actacgaatc      60
taacgcggtc acttctatag tgtcacctaa atc                                    93

<210> SEQ ID NO 164
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 164
gtaatacgac tcactatagg gagaggcggc gccgctaggg gtctctctga gactcataag      60
gccaacgatc acttctatag tgtcacctaa atc                                    93

<210> SEQ ID NO 165
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 165
gtaatacgac tcactatagg gagacggatt gtgtattggc tgtacgacgt gatcttccga      60
aagctgaaac acttctatag tgtcacctaa atc                                    93

<210> SEQ ID NO 166
<211> LENGTH: 93
<212> TYPE: DNA
<213> ORGANISM: Artificial Sequence
<220> FEATURE:

<223> OTHER INFORMATION: Oligonucleotide probe

<400> SEQUENCE: 166
gtaatacgac tcactatagg gagacggatt gtgtattggc tgtacactgg atgaaatctc    60
atgcacgaac acttctatag tgtcacctaa atc                                93

<210> SEQ ID NO 167
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 167
gtaatacgac tcactatagg gagagcagcc ggagataagc caggaactcg tataataggt    60
ccgcgaagtc acttctatag tgtcacctaa atc                                93

<210> SEQ ID NO 168
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 168
gtaatacgac tcactatagg gagagcagcc ggagataagc caggacgaag tatctgcaat    60
cgacgatctc acttctatag tgtcacctaa atc                                93

<210> SEQ ID NO 169
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 169
gtaatacgac tcactatagg gagaggtgcg gaaaccacag gcctaaccat ctcagtctaa    60
caggatgccc acttctatag tgtcacctaa atc                                93

<210> SEQ ID NO 170
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 170
gtaatacgac tcactatagg gagaaaacaa ccacagaacc acaagttgag gtgaagtact    60
aaccgaggtc acttctatag tgtcacctaa atc                                93

<210> SEQ ID NO 171
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 171
gtaatacgac tcactatagg gagaccagag gaggaagtgt aggagcaggt aagtagtcga    60
catctgcaac acttctatag tgtcacctaa atc                                93

```
<210> SEQ ID NO 172
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 172
gtaatacgac tcactatagg gagaggagga agtgtaggag caggtaacgc agaagtctag    60
gtatgcccac acttctatag tgtcacctaa atc                                93

<210> SEQ ID NO 173
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 173
gtaatacgac tcactatagg gagatcgggt cgacataacc ggatgctggc atctagacaa    60
tgaagcatgc acttctatag tgtcacctaa atc                                93

<210> SEQ ID NO 174
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 174
gtaatacgac tcactatagg gagatcgggt cgacataacc ggatgctggc aaactaaaga    60
ctgtagctgc acttctatag tgtcacctaa atc                                93

<210> SEQ ID NO 175
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 175
gtaatacgac tcactatagg gagacaaagt gaactttggt ttatctcctg caaagagtga    60
tgcaacatgc acttctatag tgtcacctaa atc                                93

<210> SEQ ID NO 176
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 176
gtaatacgac tcactatagg gagagttgta ccaaagtaca agctgagcac atacgatcgg    60
gtagatcatc acttctatag tgtcacctaa atc                                93

<210> SEQ ID NO 177
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 177
```

```
gtaatacgac tcactatagg gagaggaagc gaaaatgaaa ttgacgccat catatcaact    60
gcgataccac acttctatag tgtcacctaa atc                                 93
```

<210> SEQ ID NO 178
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 178

```
gtaatacgac tcactatagg gagaggaagc gaaaatgaaa ttgacgccca aacactctat    60
accaactctc acttctatag tgtcacctaa atc                                 93
```

<210> SEQ ID NO 179
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 179

```
gtaatacgac tcactatagg gagagctggc gtcaagccaa gagtggctgg ctaaagacaa    60
tcgaatcgac acttctatag tgtcacctaa atc                                 93
```

<210> SEQ ID NO 180
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 180

```
gtaatacgac tcactatagg gagatgccaa tgccaatgcc aagacgtcca taccaagagt    60
caagcaagtc acttctatag tgtcacctaa atc                                 93
```

<210> SEQ ID NO 181
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 181

```
gtaatacgac tcactatagg gagacctcca gtgactcagc acaggttcta tgcggagtga    60
aggagcaatc acttctatag tgtcacctaa atc                                 93
```

<210> SEQ ID NO 182
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 182

```
gtaatacgac tcactatagg gagatgggga acctgtgctg agtcactgga gtgtgatata    60
agcggagagc acttctatag tgtcacctaa atc                                 93
```

<210> SEQ ID NO 183
<211> LENGTH: 93
<212> TYPE: DNA
<213> ORGANISM: Artificial Sequence

```
<220> FEATURE:
<223> OTHER INFORMATION: Oligonucleotide probe

<400> SEQUENCE: 183
gtaatacgac tcactatagg gagaaattcc atgccatgtg tgaatccgaa gatacccagc    60
tcttcaacac acttctatag tgtcacctaa atc                                 93

<210> SEQ ID NO 184
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 184
gtaatacgac tcactatagg gagaccggat cagctgactc gcctaccaca gtaggactaa    60
tcagtgcatc acttctatag tgtcacctaa atc                                 93

<210> SEQ ID NO 185
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 185
gtaatacgac tcactatagg gagagtaata tgaaactgaa agtactgaac aagcaatgtc    60
gaatctgcgc acttctatag tgtcacctaa atc                                 93

<210> SEQ ID NO 186
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 186
gtaatacgac tcactatagg gagagtaata tgaaactgaa agtacttgga ccaagtaatc    60
ctaccacagc acttctatag tgtcacctaa atc                                 93

<210> SEQ ID NO 187
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 187
gtaatacgac tcactatagg gagaagtatg tctagactga aaaactccca acctaacgct    60
aagtcactac acttctatag tgtcacctaa atc                                 93

<210> SEQ ID NO 188
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 188
gtaatacgac tcactatagg gagagagtat gtctagactg acaatgtaca cgctcagtgg    60
tagacaagac acttctatag tgtcacctaa atc                                 93
```

-continued

<210> SEQ ID NO 189
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 189
gtaatacgac tcactatagg gagatgactg ggaaaaccct ggcgagtgaa gagctcgaat    60
cagagtctcc acttctatag tgtcacctaa atc                                93

<210> SEQ ID NO 190
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 190
gtaatacgac tcactatagg gagaacacag gaaacagcta tgactgccgc tacataggtc    60
aagaagcaac acttctatag tgtcacctaa atc                                93

<210> SEQ ID NO 191
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 191
gtaatacgac tcactatagg gagataaccc tcactaaagg gagaaaaaat ggggatgcac    60
aaacaagtac acttctatag tgtcacctaa atc                                93

<210> SEQ ID NO 192
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 192
gtaatacgac tcactatagg gagaggaatt gtgagcggat aacagctggc aaactaaaga    60
ctgtagctgc acttctatag tgtcacctaa atc                                93

<210> SEQ ID NO 193
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 193
gtaatacgac tcactatagg gagatcagac cacgtggtcg ggaaatgcta cacagaaggg    60
acaaactcgc acttctatag tgtcacctaa atc                                93

<210> SEQ ID NO 194
<211> LENGTH: 93
<212> TYPE: DNA
<213> ORGANISM: Artificial Sequence
<220> FEATURE:
<223> OTHER INFORMATION: Oligonucleotide probe

<400> SEQUENCE: 194

```
gtaatacgac tcactatagg gagatcctga ccacgtggtc ttacggatca gtcctgcaaa    60
aggctctaac acttctatag tgtcacctaa atc                                 93
```

<210> SEQ ID NO 195
<211> LENGTH: 24
<212> TYPE: DNA
<213> ORGANISM: Artificial Sequence
<220> FEATURE:
<223> OTHER INFORMATION: T7 RNA polymerase sequence

<400> SEQUENCE: 195

```
gtaatacgac tcactatagg gaga                                           24
```

<210> SEQ ID NO 196
<211> LENGTH: 24
<212> TYPE: DNA
<213> ORGANISM: Artificial Sequence
<220> FEATURE:
<223> OTHER INFORMATION: SP6 RNA polymerase binding site

<400> SEQUENCE: 196

```
cacttctata gtgtcaccta aatc                                           24
```

<210> SEQ ID NO 197
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 197

```
gtaatacgac tcactatagg gagaagaggg gactttccga gaggtccaag gctgatacat    60
cctctggttc acttctatag tgtcacctaa atc                                 93
```

<210> SEQ ID NO 198
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 198

```
gtaatacgac tcactatagg gagaagaggg gactttccga gagggaggag atgtggggtc    60
ttaatgctgc acttctatag tgtcacctaa atc                                 93
```

<210> SEQ ID NO 199
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 199

```
gtaatacgac tcactatagg gagaagaggg gactttccga gaggcaagac aaaatacctg    60 caagagggggc acttctatag tgtcacctaa atc                                93
```

<210> SEQ ID NO 200
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 200
gtaatacgac tcactatagg gagaagaggc gactttccga gaggacattc caaacaagac    60
gctgttgtgc acttctatag tgtcacctaa atc    93

<210> SEQ ID NO 201
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 201
gtaatacgac tcactatagg gagaagaggc gactttccga gagggggaagc tggagcacag    60 aagttgtctc acttctatag tgtcacctaa atc    93

<210> SEQ ID NO 202
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 202
gtaatacgac tcactatagg gagaagaggc gactttccga gaggatttcg ttatcggaga    60
aggagagggc acttctatag tgtcacctaa atc    93

<210> SEQ ID NO 203
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 203
gtaatacgac tcactatagg gagagatcta ggtcactgtg accctaggag ggctgatgat    60
agtgccattc acttctatag tgtcacctaa atc    93

<210> SEQ ID NO 204
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 204
gtaatacgac tcactatagg gagagatcta ggtcactgtg accctgtctt taacatttgc    60
aatgggctgc acttctatag tgtcacctaa atc    93

<210> SEQ ID NO 205
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 205
gtaatacgac tcactatagg gagagatcta ggtcactgtg accccgaaat ggtttattac    60
aaggcagccc acttctatag tgtcacctaa atc    93

<210> SEQ ID NO 206
<211> LENGTH: 93

```
<212> TYPE: DNA
<213> ORGANISM: Artificial Sequence
<220> FEATURE:
<223> OTHER INFORMATION: Synthetic oligonucleotide

<400> SEQUENCE: 206
gtaatacgac tcactatagg gagagatcta gtacactgta acccggagat gatatcaata    60
ggcttgcggc acttctatag tgtcacctaa atc                                 93

<210> SEQ ID NO 207
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 207
gtaatacgac tcactatagg gagagatcta gtacactgta acccgcacat ggctgtgaat    60
gaaaggatac acttctatag tgtcacctaa atc                                 93

<210> SEQ ID NO 208
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 208
gtaatacgac tcactatagg gagagatcta gtacactgta acccctttcaa gtctccattt   60 ccagatgggc acttctatag tgtcacctaa atc                                 93

<210> SEQ ID NO 209
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 209
gtaatacgac tcactatagg gagaattcga tcggggcggg gcgaagtttg agttgagagc    60
agtcctcggc acttctatag tgtcacctaa atc                                 93

<210> SEQ ID NO 210
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 210
gtaatacgac tcactatagg gagaattcga tcggggcggg gcgagcaaga cagctacagc    60
atcgacatcc acttctatag tgtcacctaa atc                                 93

<210> SEQ ID NO 211
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 211
gtaatacgac tcactatagg gagaattcga tcggggcggg gcgacaagtg tctcccaata    60
```

```
tgaggtgcac acttctatag tgtcaccta atc                                    93

<210> SEQ ID NO 212
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 212
gtaatacgac tcactatagg gagaattcga tcggttcggg gcgatgtgtg tatctgagcc      60
attgaagggc acttctatag tgtcaccta atc                                    93

<210> SEQ ID NO 213
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 213
gtaatacgac tcactatagg gagaattcga tcggttcggg gcgaaactgt gtcctagccc      60
gcatattgtc acttctatag tgtcaccta atc                                    93

<210> SEQ ID NO 214
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 214
gtaatacgac tcactatagg gagaattcga tcggttcggg gcgagcctgg ccatatctca      60
aagttgttcc acttctatag tgtcaccta atc                                    93
```